(12) United States Patent
Lefebvre et al.

(10) Patent No.: US 9,327,213 B2
(45) Date of Patent: May 3, 2016

(54) PREPARATIVE CHROMATOGRAPHY COLUMN

(71) Applicant: Bio-Rad Laboratories, Inc., Hercules, CA (US)

(72) Inventors: Sébastien Lefebvre, Saint Beauzire (FR); Lilian Portier, Paslières (FR); Maurice Agée, Yssac-la-Tourette (FR)

(73) Assignee: Bio-Rad Laboratories, Inc., Hercules, CA (US)

( * ) Notice: Subject to any disclaimer, the term of this patent is extended or adjusted under 35 U.S.C. 154(b) by 274 days.

(21) Appl. No.: 13/771,371

(22) Filed: Feb. 20, 2013

(65) Prior Publication Data

US 2013/0228501 A1 Sep. 5, 2013

Related U.S. Application Data

(60) Provisional application No. 61/601,904, filed on Feb. 22, 2012.

(51) Int. Cl.
| | | |
|---|---|---|
| *B01D 15/22* | (2006.01) | |
| *B01D 15/20* | (2006.01) | |
| *B65B 1/24* | (2006.01) | |
| *G01N 30/60* | (2006.01) | |
| *F16L 11/00* | (2006.01) | |

(Continued)

(52) U.S. Cl.
CPC .............. *B01D 15/22* (2013.01); *B01D 15/206* (2013.01); *B65B 1/24* (2013.01); *F16L 11/00* (2013.01); *F16L 33/00* (2013.01); *G01N 30/6021* (2013.01); *G01N 30/6082* (2013.01); *G01N 30/603* (2013.01); *Y10T 29/49865* (2015.01)

(58) Field of Classification Search
None
See application file for complete search history.

(56) References Cited

U.S. PATENT DOCUMENTS

| | | | | |
|---|---|---|---|---|
| 4,250,035 A | * | 2/1981 | McDonald et al. .... | B01D 15/08 206/305 |
| 4,280,905 A | * | 7/1981 | Gunkel et al. ............. | 210/198.2 |

(Continued)

FOREIGN PATENT DOCUMENTS

| | | |
|---|---|---|
| CN | 1736536 A | 2/2006 |
| EP | 0 023 582 A1 | 2/1981 |

(Continued)

OTHER PUBLICATIONS

International Search Report and Written Opinion from PCT/US2013/026859, dated Jun. 17, 2013.

(Continued)

*Primary Examiner* — Katherine Zalasky
*Assistant Examiner* — Kara Graber
(74) *Attorney, Agent, or Firm* — Kilpatrick Townsend & Stockton LLP

(57) ABSTRACT

A chromatography column design and a packing device, as well as a method for obtaining a column with a very compact and uniform bed are provided. The bed remains compact and uniform during operation of the column and during sanitization, storage and transportation of the column. The amount of hardware, particularly the hardware parts in contact with product, is minimized, especially with the implementation of an internal liner. With this internal liner, the packed bed can be separated from the column in intact form, or even prepared separately from, and outside of, the column.

10 Claims, 24 Drawing Sheets

(51) Int. Cl.
*F16L 33/00* (2006.01)
*B01D 15/08* (2006.01)

(56) References Cited

U.S. PATENT DOCUMENTS

| | | | |
|---|---|---|---|
| 5,021,162 A * | 6/1991 | Sakamoto et al. | 210/635 |
| 2002/0153312 A1 * | 10/2002 | Gjerde et al. | 210/635 |
| 2002/0166816 A1 | 11/2002 | Allen et al. | |
| 2004/0035774 A1 | 2/2004 | Horsman et al. | |
| 2006/0049090 A1 | 3/2006 | Spoldi et al. | |
| 2007/0090035 A1 | 4/2007 | Rahn et al. | |
| 2009/0065415 A1 | 3/2009 | Vetter et al. | |
| 2010/0206813 A1 | 8/2010 | Yukon | |
| 2011/0139718 A1 | 6/2011 | Snyder | |

FOREIGN PATENT DOCUMENTS

| | | | |
|---|---|---|---|
| GB | 2 440 244 B | 6/2009 | |
| WO | 95/27547 A1 | 10/1995 | |
| WO | 2009/041877 A1 | 4/2009 | |
| WO | 2011/076386 A1 | 6/2011 | |
| WO | WO 2012040574 A1 * | 3/2012 | G01N 30/56 |

OTHER PUBLICATIONS

Extended European Search Report from EP Appl. No. 13752450.0, dated Sep. 21, 2015.

* cited by examiner

PREPARATIVE CHROMATOGRAPHY COLUMN

CROSS-REFERENCE TO RELATED APPLICATION

This application claims the benefit of U.S. Provisional Patent Application No. 61/601,904, filed Feb. 22, 2012, the contents of which are incorporated herein by reference in their entirety.

BACKGROUND OF THE INVENTION

1. Field of the Invention

This invention relates to preparative chromatography columns, i.e., chromatography columns in which molecular species are extracted from source solutions in high amounts for commercial use rather than for analytical purposes.

2. Description of the Prior Art

The chromatography columns to which the present invention is primarily directed are preparative chromatography columns designed for plug flow of a mobile phase through a packed bed of solid or semi-solid stationary phase made from soft (semi-solid) or rigid (solid) particles. The typical such column is a cylinder closed at each end by plates, each plate equipped with a fluid port, a distribution system, and a filter. The cylinder is uniformly filled with a separation medium or media, packed to form a "bed." The filters have pore sizes that are smaller than the particle size of the media to retain the media within the cylinder, and yet large enough to allow the process liquids (i.e., the mobile phase) to pass through the filters and hence the column. The distribution system ensures that the process liquid is spread across the full width of the bed, thereby making maximal use of the bed.

The typical preparative chromatography column is large enough in diameter that separation within the column can be performed at a commercially useful throughput rate, i.e., one that will produce the extracted species at an economically viable production rate. The typical column is also small enough in depth that the pressure drop through the column is low, thereby avoiding the need for a high pump pressure to force the mobile phase through the column. There must be sufficient depth however to provide the mobile phase with a residence time that is long enough to allow proper interaction between the mobile and stationary phases. The typical column also contains a plunger or piston head that is lowered to contact and compress the stationary phase to a desired height. In operation, the mobile phase enters the column at the top through the plunger which includes a distributor plate to spread the mobile phase across the full width of the bed, thereby making maximal use of the bed.

The performance of a preparative chromatography column of the type described above is very sensitive to the degree of uniformity of the stationary phase. Optimal operation is achieved when the bed is homogeneous, compact, and of uniform depth such that the mobile phase is evenly distributed across the width of the bed. In the present state of art, the need for a stationary phase that is adjustable yet stable during purification, sanitization, storage and transportation of the column has led to columns with adjustable mechanical assemblies. Sealing between parts of the column, especially between the plunger and the column tube or between the bottom plate and the tube, requires tight adjustment of the parts, close alignment of the parts, and a smooth interior surface of the column tube. In addition, particularly in columns that are used for purifying food or drugs, the parts of the column that are in contact with the product, including the tube itself, the plates, and the distributors, must be made of special materials that are stable and inert, i.e., that neither leach into the product nor corrode upon contact with the product. As a consequence, the number of column parts, the volume of the column, the materials from which the parts are made, and the dimensional precision of the parts, make the column expensive and thus not suitable for single-use applications. The use of other forms of media, such as membranes or monoliths, could be simpler and less expensive but often fail to provide the same degree of purification.

The transportation of packed columns on long distances, for instance with the pre-packed or disposable columns applications, is also a challenge for maintaining the performance of the column. All the packing methods which only use downwards strengths, such as flow circulation and axial compression for column packing, succeed to settle the media particles in some kind of equilibrium after a short or long period, where each particle finds support on the lower particles. But this arrangement might not be optimal: excessive voids can still take place due to the friction of the tube walls, or due to the difference in size and shape of particles. The random stacking of these particles is also not optimal: the vibration, shocks and tilting and thermal variations during the transportation often induce local re-arrangements of the particles resulting with further compression of the bed, forming of supernatant, initiation of bed cracking. This prevents the transportation of packed columns on long distances, especially when non compressible chromatography media is used, where the bed is not maintained under compression.

SUMMARY OF THE INVENTION

It has now been discovered that the problems cited above can be addressed and at least partially mitigated by a specific design of the column, a special packing device and a specific packing method. This design can be significantly simplified and reduced in cost in some embodiments by the use of a liner inside the chromatography column. The liner can be, for example, a tubular and flexible water-impermeable film that will contain the separation media and allow movement of the piston within the liner. This configuration allows the media in the form of either a slurry or dry particles to be packed with the packing method described hereafter into a compact and uniform bed, and keeps the bed compact and uniform during operation of the column and during transportation. Use of the liner also promotes and enhances sanitization, storage and transportation of the column, and uses a minimal amount of hardware, particularly the hardware parts that will be in contact with the product. Use of the liner also allows the packed bed to be separated from the column. In some embodiments, the liner is transparent, allowing a user to readily see the contents within the liner. The rigid external shell containing the liner can in different embodiments be transparent or not.

Further advantages include the ability to separate contaminated waste from non contaminated waste, in the case of disposable columns, and the better stability of the packed bed over a large number of cycles, thanks to the packing method described Also provided is a packing method and apparatus able to obtain very high performance and reproducible packing, in terms of bed height and particles arrangement. This objective is obtained by the conjunction of a precise dosing of the media and the packing method combining flow packing and rhythmic (percussive) packing While this aspect can be used with a column liner as described above, the inclusion of a liner with the packing method is optional. In some embodiments in which the percussive packing is used, the chromatography resin (i.e., the separation medium material) is rigid or semi-rigid, e.g., such as a ceramic apatite (including but not limited to hydroxyapatite and fluoroapatite) or silica.

Also provided herein is a new method of applying and tightening a filter in the bore hole of a piston or a bore hole in the bottom plate of the column. The method involves heating the piston and/or column such that the area for the filter thermally expands. Eventually the filter can be cooled to shrink its outer diameter. The filter is then added and the piston and/or column is allowed to cool to ambient temperature, while the filter warms up to ambient temperature thereby tightening the area tightly around the filter, thereby affixing the filter to cover the bore hole.

In some embodiments, a chromatography column is provided comprising: a rigid column shell, a bottom plate secured to the column shell and comprising a layer of porous material over a rigid and liquid-impermeable base and the base has a port therein for passage of liquid, a piston comprising a layer of porous material over a rigid and liquid-impermeable base and the base having a port therein for passage of liquid, the piston fitting within a tube within the column shell, and the tube being of flexible, water-impermeable material containing a packed bed of separation medium, the tube being open at a first end, closed at a second end with the bottom plate, and encircling the piston.

In some embodiments, the column further comprises a releasable seal between the tube to the piston. In some embodiments, the piston comprises the seal. In some embodiments, the rigid column shell comprises the seal. In some embodiments, the seal is selected from the group consisting of an O-ring, a lobe joint, and a scraper seal.

In some embodiments, the piston fits within the column shell with clearance between the piston and the column shell to allow liquid to flow past the piston and thereby equalize pressure above and below the piston when the piston is moved within the column shell.

In some embodiments, the flexible, water-impermeable material is elastic.

In some embodiments, the layer of porous material on the bottom plate is planar and the base has a concave upper surface tapering toward the port in the base, whereby the layer of porous material contacts the base along a periphery of the base while leaving a gap between the layer and the base inside the periphery. In some embodiments, the layer of porous material on the piston is planar and the piston has a concave surface facing the layer of porous material and tapering toward the port in the piston, whereby the layer of porous material contacts the concave surface along a periphery of the concave surface while leaving a gap between the layer and the concave surface inside the periphery.

In some embodiments, the layer of porous material on the bottom plate is planar and the base has a concave upper surface tapering toward the port in the base, whereby the layer of porous material contacts the base along a periphery of the base while leaving a gap between the layer and the base inside the periphery, and the layer of porous material on the piston is planar and the piston has a concave surface facing the layer of porous material and tapering toward the port in the piston, whereby the layer of porous material of the piston contacts the concave surface of the piston along a periphery of the concave surface while leaving a gap between the layer and the concave surface inside the periphery.

In some embodiments, the column further comprises a column shell extension removably attachable to the column shell to extend the height of the column shell, and wherein the tube of flexible, water-impermeable material is of sufficient length to extend through both the column shell and the column shell extension, the column shell extension being of sufficient width to receive the piston with clearance between the piston and the extension to allow liquid to flow past the piston and thereby equalize pressure above and below the piston when the tube of flexible, water-impermeable material is within both the column shell and the column shell extension and the piston is moved within the tube. In some embodiments, the column further comprises a cap that attaches to the column shell extension and that supports the piston, and means for securing the first end of the tube of flexible, water-impermeable material to the cap. In some embodiments, the column further comprises a slurry injection port allowing for injection of a slurry of chromatography media under the piston in the column.

In some embodiments, the column further comprises under the base, a percussion table capable of rhythmically tapping the base to improve packing of particles of a separation medium in the column.

In some embodiments, the chromatography column is a preparative chromatography column.

Also provided are methods of packing a chromatography column. In some embodiments, the method comprises: (a) placing a tube of flexible, water-impermeable material in a rigid column shell, the tube being open at a first end and closed at a second end with a bottom plate comprising a layer of porous material over a rigid and liquid-impermeable base, the layer of porous material facing the first end of the tube and the base having a port therein for discharge of liquid; (b) placing a slurry of separation medium particles in the tube within the column shell and placing a piston in the tube over the slurry, the piston having a layer of porous material facing the slurry and a port for supply of liquid over the layer of porous material; (c) exerting a downward circulation of liquid between the piston and the bottom plate to settle and compact the slurry; and (d) lowering the piston over the slurry to compact the particles into a packed bed.

In some embodiments, the method further comprises assisting packing of the slurry with percussive tapping from under the base. In some embodiments, the percussive tapping occurs at a frequency from 0.2 to 100 Hz with an amplitude less than 5 mm.

In some embodiments, the method further comprises attaching a column shell extension to the column shell to extend the height of the column shell prior to placing the tube of flexible, water-impermeable material in the column shell, and wherein: step (a) comprises placing the tube of flexible, water-impermeable material in both the column shell and the column shell extension; step (b) comprises placing a sufficient quantity of the slurry within the tube to extend into both the column shell and the column shell extension; step (c) comprises compacting all of the particles into a portion of the tube within the column shell; the method further comprising: (d) removing the column shell extension after step (c) to leave the column shell containing the packed bed.

In some embodiments, the method further comprises closing the top of the column shell extension with a cap that supports the piston, and for securing the first end of the tube of flexible, water-impermeable material to the cap, prior to step (c).

In some embodiments, the method further comprises: (e) severing the tube of flexible, water-impermeable material above the packed bed to leave a shortened length of the tube encircling the packed bed.

In some embodiments, the layer of porous material on the bottom plate is planar and the base has a concave upper surface tapering toward the port in the base, whereby the layer of porous material contacts the base along a periphery of the base while leaving a gap between the layer and the base inside the periphery.

In some embodiments, the layer of porous material on the piston is planar and the piston has a concave surface facing the layer of porous material and tapering toward the port in the piston, whereby the layer of porous material contacts the concave surface along a periphery of the concave surface while leaving a gap between the layer and the concave surface inside the periphery.

Also provided is a tube of flexible, water-impermeable material open at a first end and closed at a second end with a bottom plate comprising a layer of porous material over a rigid and liquid-impermeable base, the layer of porous material facing the first end of the tube and the base having a port therein for passage of liquid. In some embodiments, the flexible, water-impermeable material is elastic. In some embodiments, the layer of porous material is planar and the base has a concave upper surface tapering toward the port, whereby the layer contacts the base along a periphery of the base while leaving a gap between the layer and the base inside the periphery.

Also provided is a chromatography column (including or optionally lacking a liner). In some embodiments, the column comprises: a rigid water-impermeable column shell containing a packed bed of separation medium, the shell forming a tube being open at a first end, closed at a second end with a bottom plate, and encircling a piston, the shell or piston comprising a port for supply of liquid; the bottom plate secured to the column shell and comprising a layer of porous material over a rigid and liquid-impermeable base and the base having a port therein for passage of liquid, and the piston fitting within the shell and comprising a seal between the piston and the shell.

In some embodiments, the seal is selected from the group consisting of an O-ring, a lobe joint, and a scraper seal. In some embodiments, the piston comprises the seal. In some embodiments, the rigid column shell comprises the seal.

In some embodiments, the layer of porous material on the bottom plate is planar and the base has a concave upper surface tapering toward the port in the base, whereby the layer of porous material contacts the base along a periphery of the base while leaving a gap between the layer and the base inside the periphery.

In some embodiments, the layer of porous material on the piston is planar and the piston has a concave surface facing the layer of porous material and tapering toward the port in the piston, whereby the layer of porous material contacts the concave surface along a periphery of the concave surface while leaving a gap between the layer and the concave surface inside the periphery.

In some embodiments, the layer of porous material on the bottom plate is planar and the base has a concave upper surface tapering toward the port in the base, whereby the layer of porous material contacts the base along a periphery of the base while leaving a gap between the layer and the base inside the periphery, and the layer of porous material on the piston is planar and the piston has a concave surface facing the layer of porous material and tapering toward the port in the piston, whereby the layer of porous material of the piston contacts the concave surface of the piston along a periphery of the concave surface while leaving a gap between the layer and the concave surface inside the periphery.

In some embodiments, the column further comprises a column water-impermeable shell extension attachable to the column shell to water-impermeably extend the height of the column shell, and wherein the shell extension being of sufficient width to receive the piston with clearance between the piston and the extension to allow liquid to flow past the piston and thereby equalize pressure above and below the piston. In some embodiments, the column further comprises a cap that attaches to the column shell extension and that supports the piston. In some embodiments, the column further comprising a slurry injection port which can be used to inject a slurry of chromatography media under the piston in the column.

In some embodiments, the chromatography column is a preparative chromatography column.

Also provided is a method of packing a preparative chromatography column as described above. In some embodiments, the method comprises: (a) placing a slurry of separation medium particles in the column shell closed on bottom end with the bottom plate and placing a piston in the column shell over the slurry, (b) closing the top of the column shell extension with a cap that supports the piston; (c) exerting a downward circulation of liquid between the piston and the bottom plate to settle and compact the slurry; (d) lowering the piston over the slurry to compact the particles into a packed bed; and (e) removing the column shell extension after step (d) to leave the column shell containing the packed bed. In some embodiments, the column further comprises under the base, a percussion table capable of rhythmically tapping the base to improve packing of particles of a separation medium in the column.

In some embodiments, the rigid column shell and the tube of flexible, water-impermeable material are sufficiently high to contain the media in suspension (slurry), further comprising a piston with a gasket or protuberance to seal the tube to the piston all along the tube.

Also provided are methods of attaching a filter to a bore hole in a bottom plate of a chromatography column and/or a bore hole in a piston for packing a chromatography column. In some embodiments, the method comprises: heating the bottom plate and/or piston such that an opening comprising the bore hole expands; placing a filter into the heated opening; and allowing the bottom plate and/or piston to cool, thereby contracting the opening such that the filter is fixed in the opening.

In some embodiments, the filter placed into the heated opening is cooled below ambient temperature such that the filter expands upon returning to ambient temperature.

In some embodiments, the method further comprises fastening the filter to the bottom plate and/or piston at least one position on the filter aside from the filter edge. In some embodiments, the fastening comprises adding one or more screw through the filter and into the bottom plate and/or piston.

Further features, aspects, objects, and advantages of the invention will be apparent from the description that follows.

DETAILED DESCRIPTION OF SELECTED EMBODIMENTS

Figure 12:
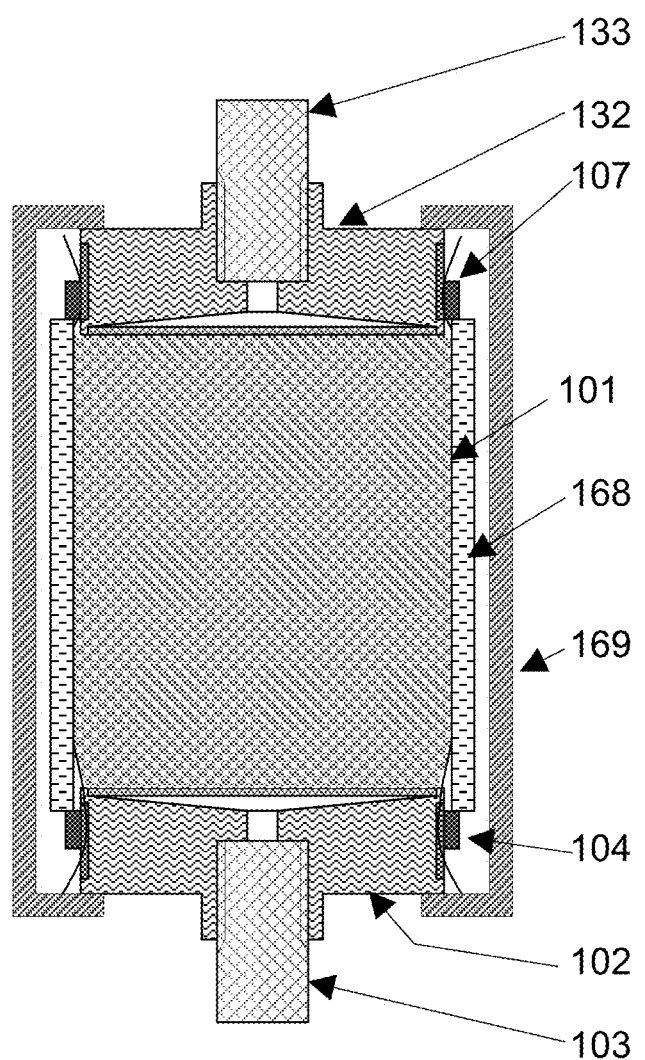
FIG. 12 is a cross section of a cartridge incorporating the separation medium, the liner, and an outer tube.
Figure 13:
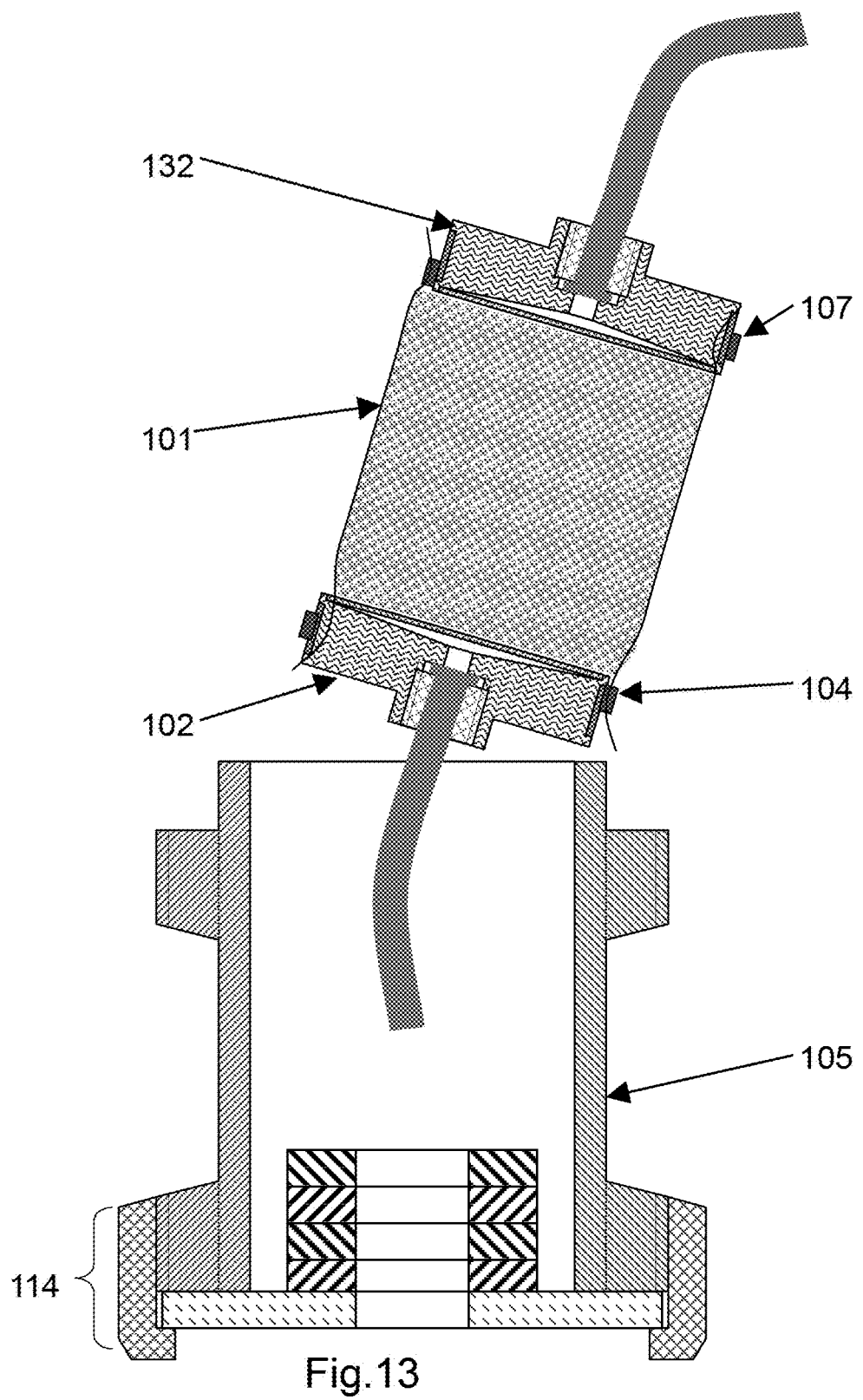
FIG. 13 is a cross section view of the dismantling of the column of the preceding Figures.
Figure 14:
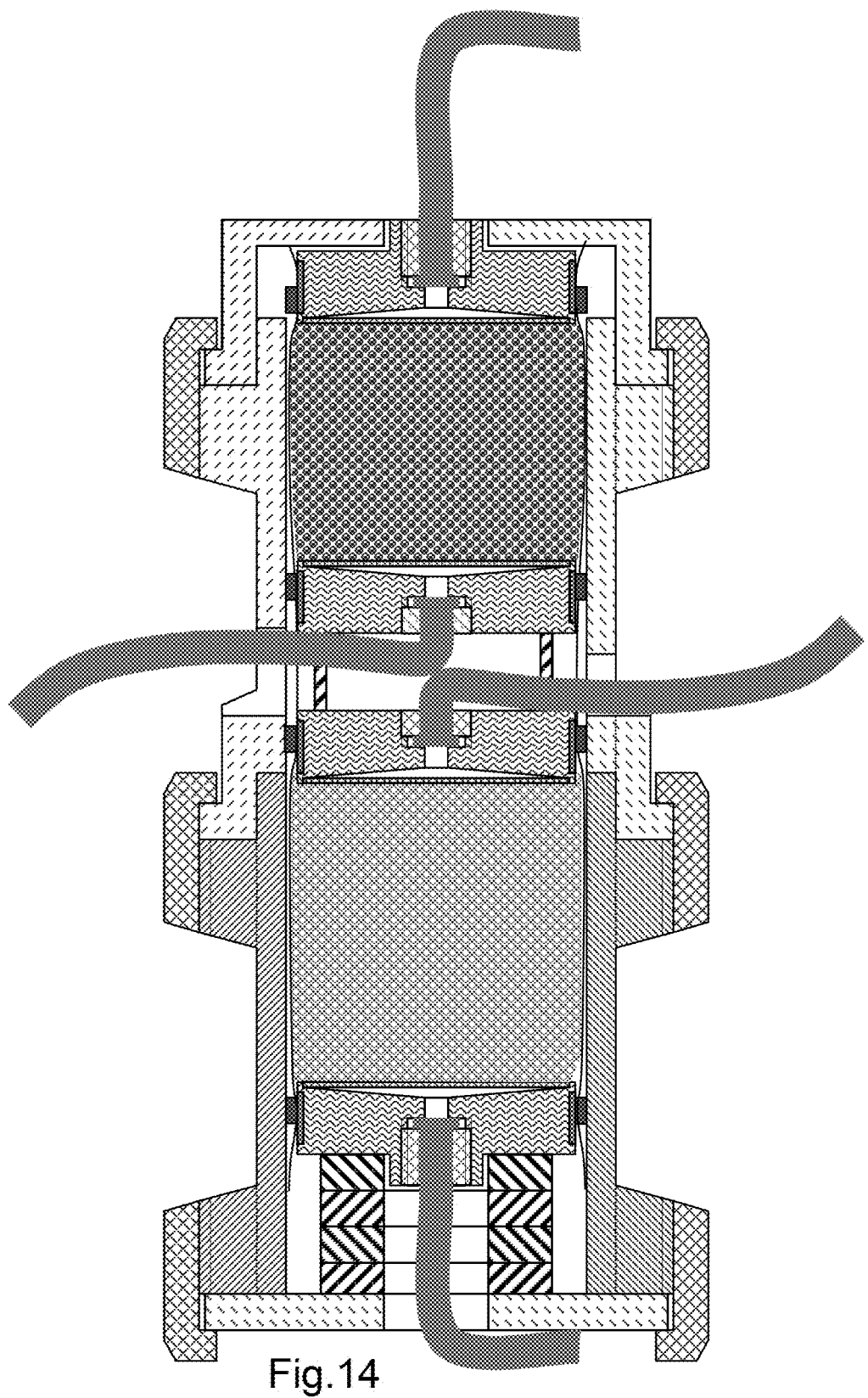
FIG. 14 is a cross section view of an arrangement of stacked columns, each column of the stack being of the construction of those in the preceding Figures.
Figure 15:
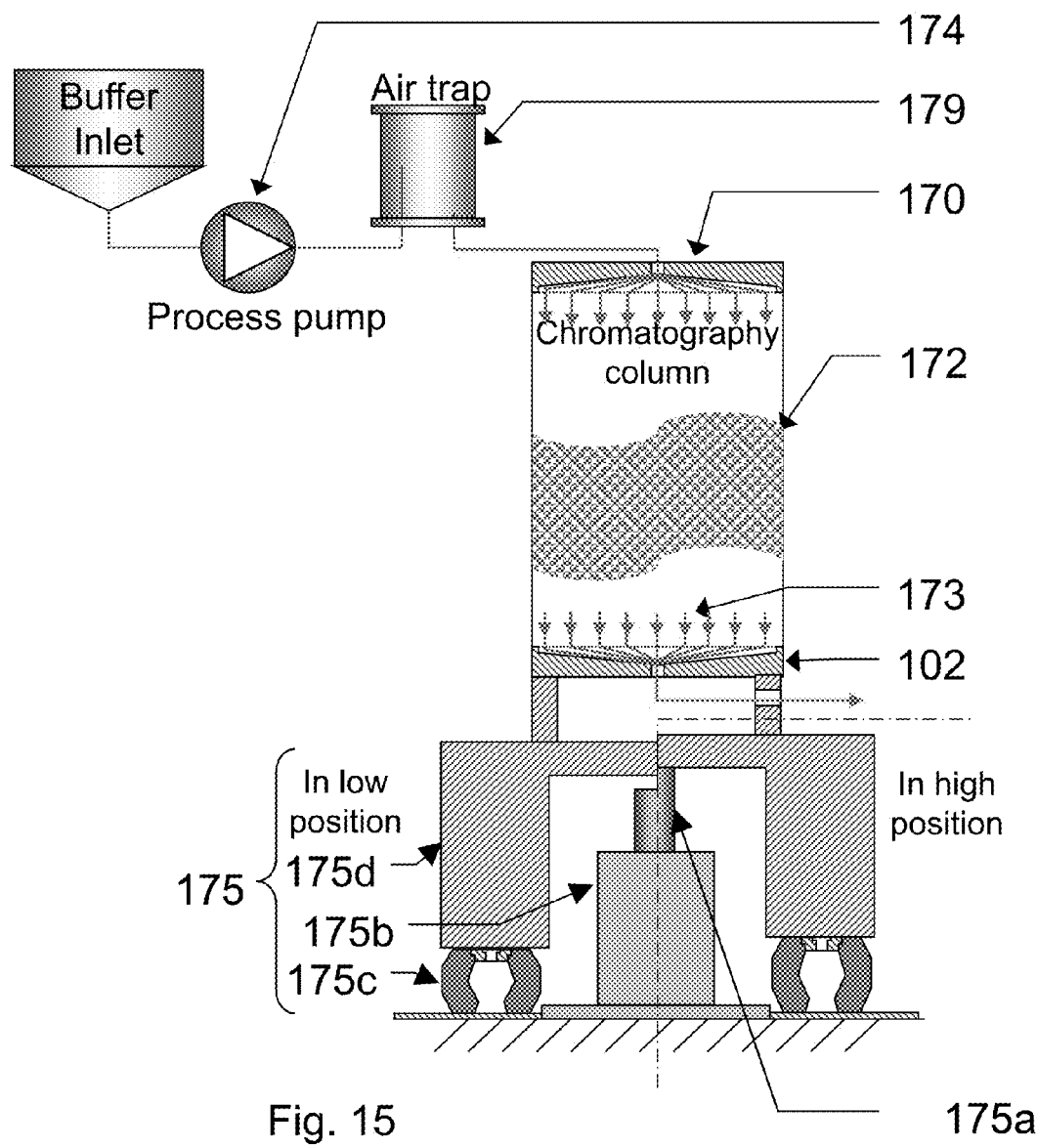
FIG. 15 is a schematic of the installation needed for the packing of the column.
Figure 16:
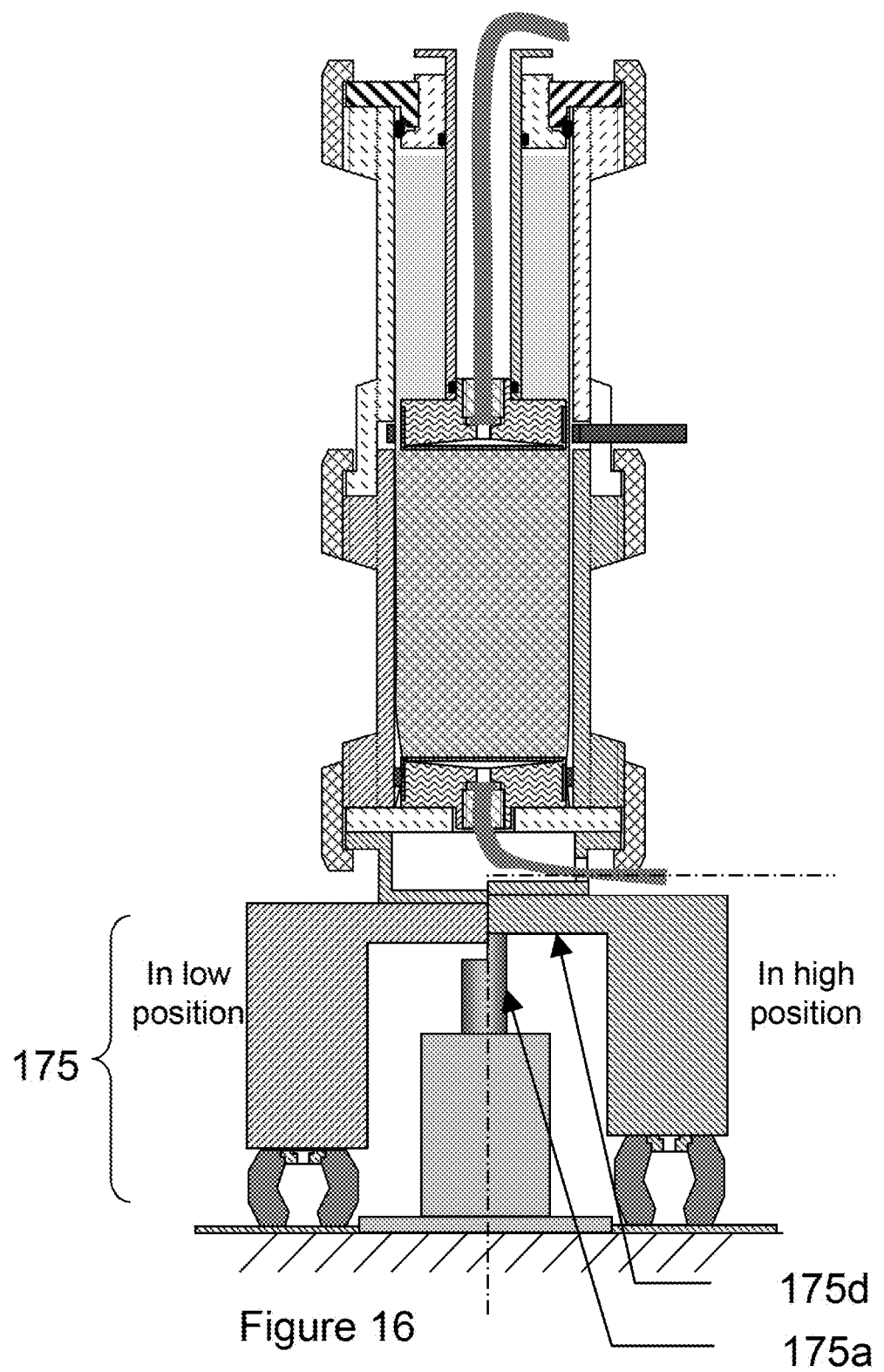
FIG. 16 is the same view as FIG. 5, showing the percussion table.
Figure 17:
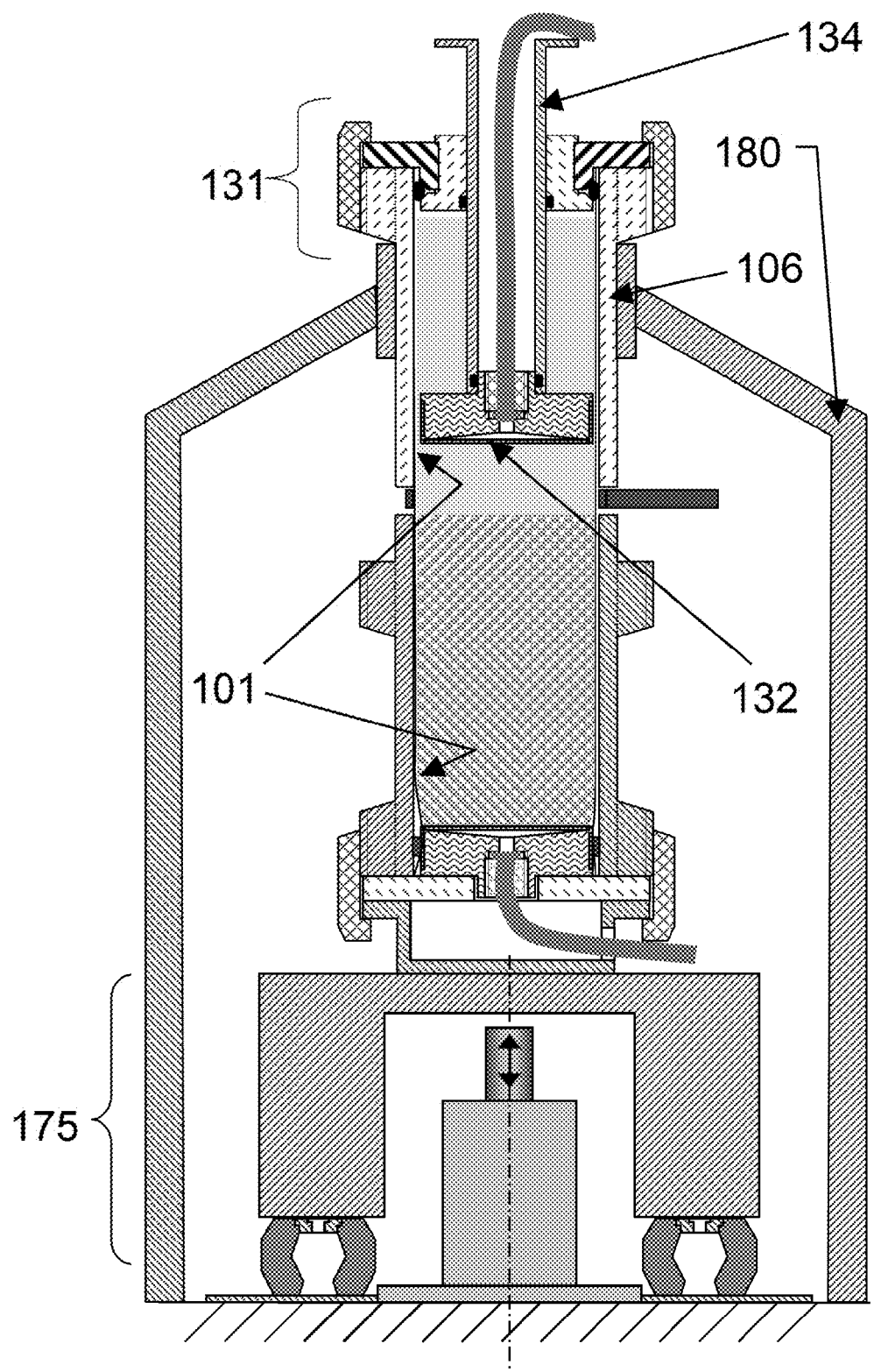
FIG. 17 is the same view as FIG. 16, where the tube extension is supported by a separate frame.
Figure 18:
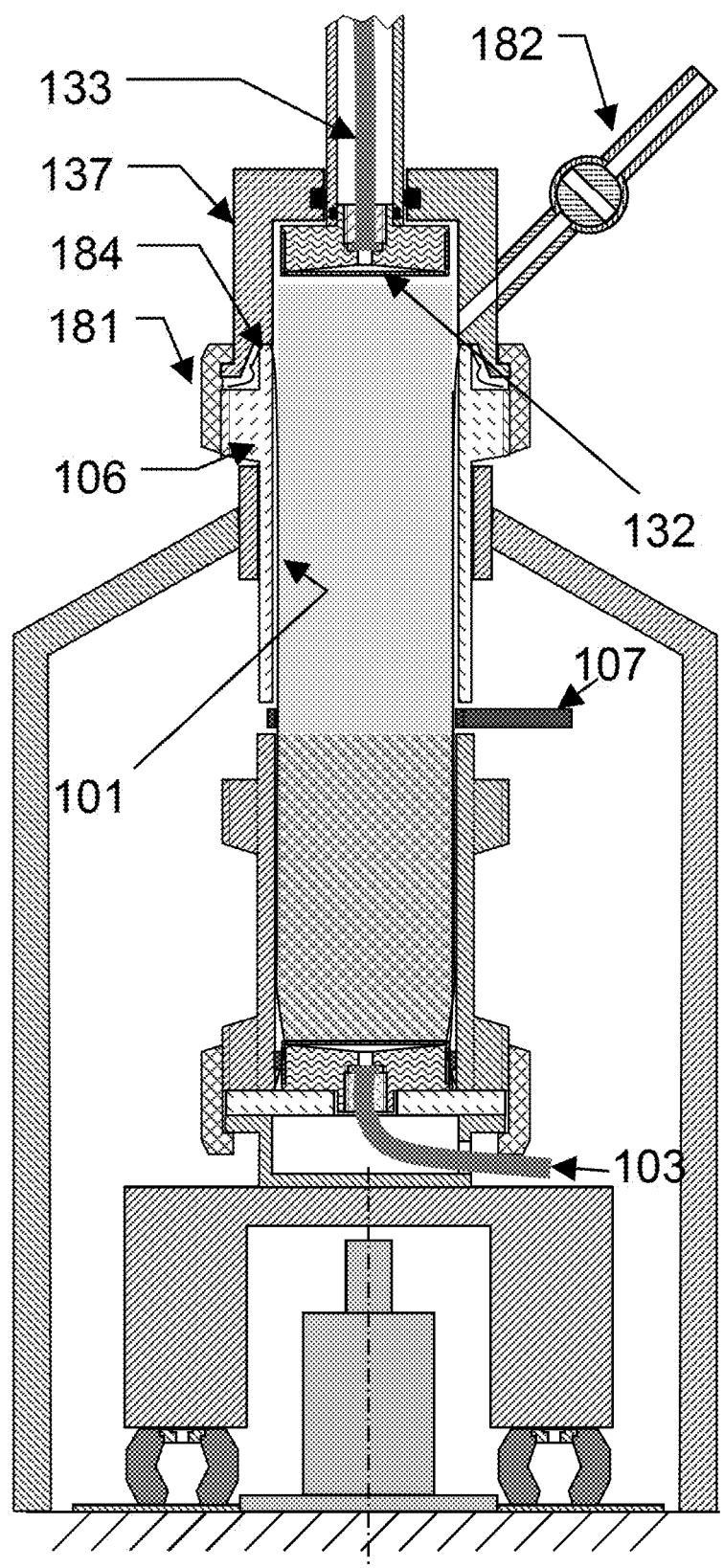
FIG. 18 is the same view as FIG. 17, with different solution for the holding of liner, and with a slurry injection valve.
Figure 19:
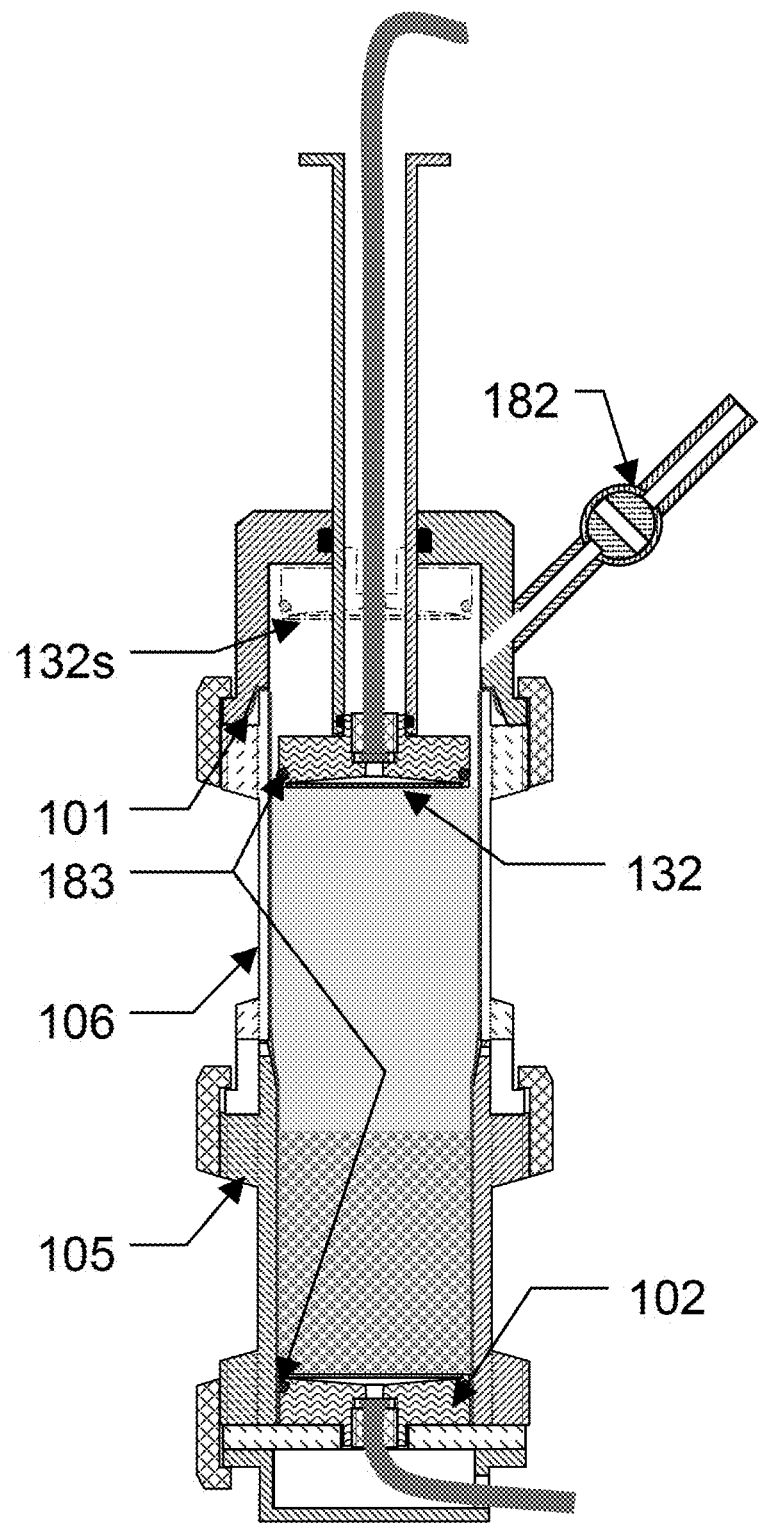
FIG. 19 shows an alternative solution for the design of the column and packing system where the external clamp is replaced by an O-ring on the piston.
Figures 20, 20A:
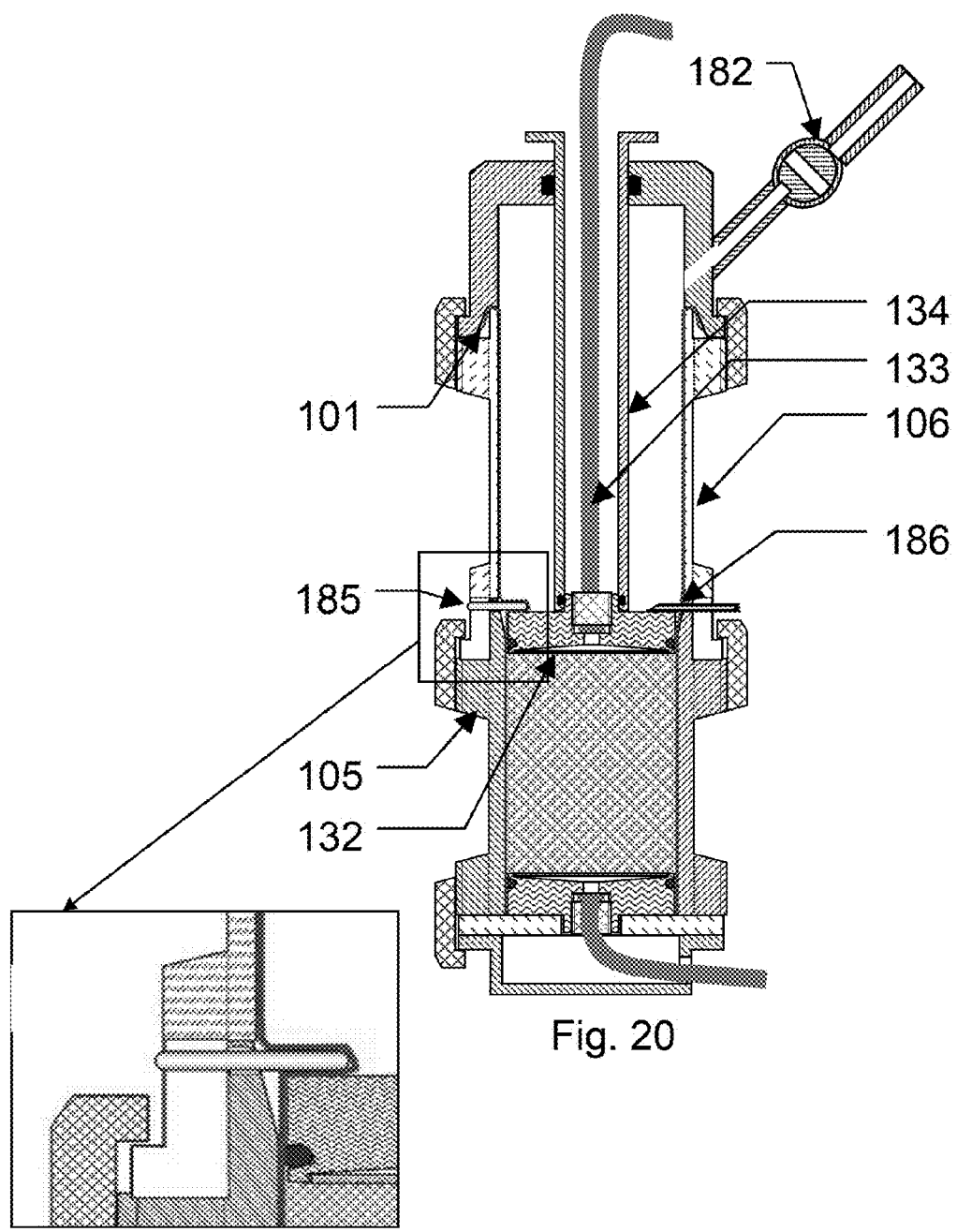
FIG. 20 is the same view as FIG. 19, after the piston is lowered against the bed.
FIG. 20A is a magnified view of FIG. 20 depicting the piston lowered against the bed.

FIGS. 1 to 11 depict one illustrative embodiment of the invention and show the stepwise transformation of the column from an empty condition to a packed column. These pictures focus on the column design, without any details on the packing apparatus. The succession of figures illustrates the different parts of the column, methods of assembly and disassembly, and the advantages of the invention. FIGS. 12 through 14 show variations on the embodiment of FIGS. 1 to 11. FIGS. 15 to 18 focus on the packing apparatus: FIG. 15 showing the principle of the installation and FIGS. 16 to 18 showing variations of the design related to the packing method. FIGS. 19 to 20 depict one alternative embodiment of the embodiment of FIGS. 5 to 11 and show the stepwise transformation for obtaining a packed column. It is understood however that the invention as a whole is not restricted to the constructions shown in these Figures or the description below of their use.

Figure 1:
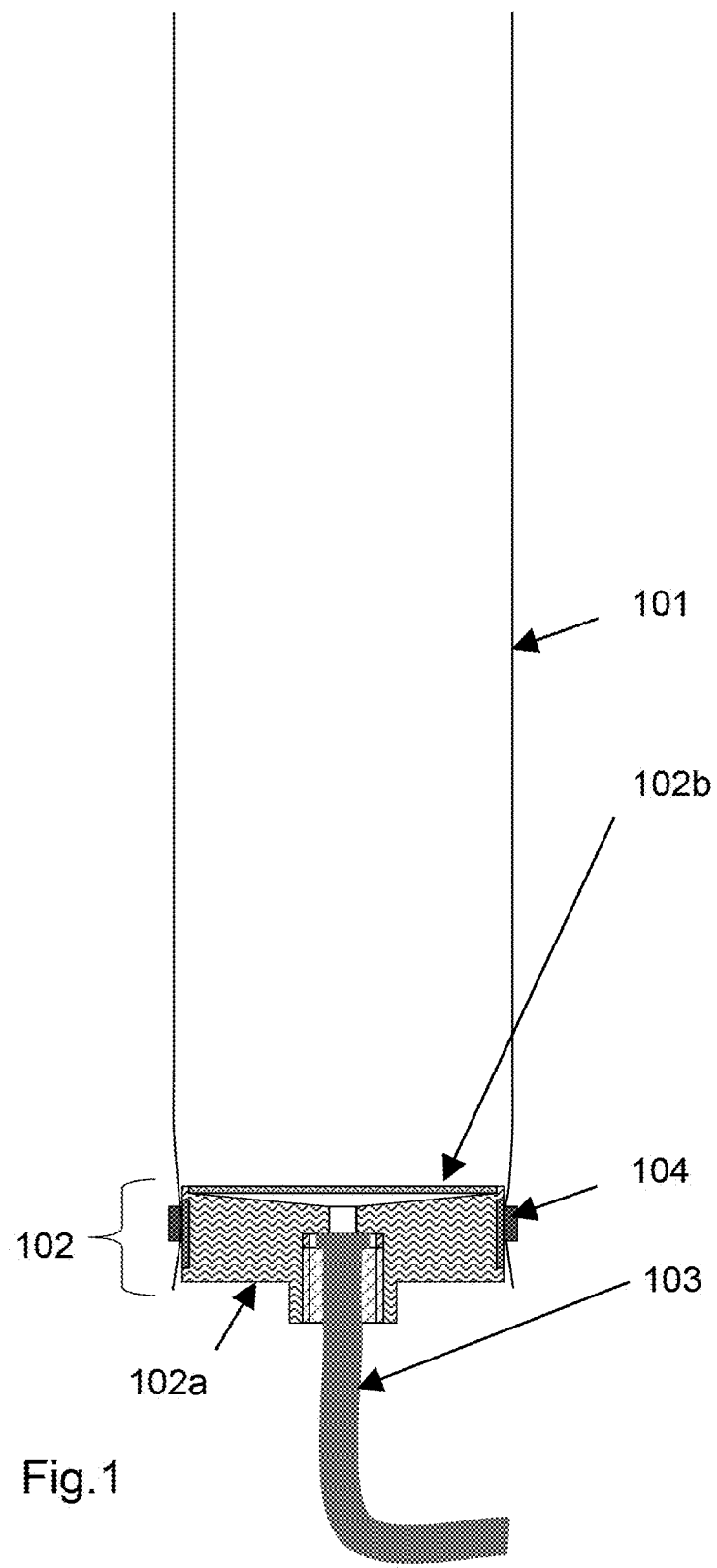
FIG. 1 is a cross section of a tubular liner attached to a bottom plate. This and all other figures herein are within the scope of the present invention.

FIG. 1 depicts a tubular and flexible water-impermeable film 101 of a plastic material such as low-density polyethylene or any polymer of similar physical characteristics. The tubular film is open at one end (i.e., the top end in the view shown in the Figure) and closed at the other end by a bottom plate 102, in this case by the tubular film being placed around the outer edge of a bottom plate. The bottom plate 102 contains rigid and liquid-impermeable base 102a which serves as a mobile phase distributor, with a layer of porous material 102b on the upper side of the distributor. A bottom process port 103 extends from the lower side of the distributor, for discharge of liquid from the column. In the embodiment shown in FIG. 1, the bottom plate 102 is surrounded with a ring 104 to secure the film 101 around the bottom plate in a fluid-tight manner. Tightening of the ring 104 can be achieved by using a ring of elastomeric material, or by a clamp, a collar, a wire, or any other device or means that will form a hermetic seal between the bottom plate and the plastic film. The seal can also be formed by an adhesive or by welding. Another solution is also further described with FIG. 19. In this embodiment, the layer of porous material 102b is planar and the base 102a has a concave upper surface tapering toward the bottom port 103, leaving a gap between the porous layer and the base for collection of the liquid and avoidance of dead volume.

The inner diameter of the tube 101, without the securing ring 104, can be equal to or slightly larger than the bottom plate 102, or smaller but sufficiently elastic so as to expand under further hydraulic pressure. The length of the tube 101 is great enough that the interior volume of the tube will contain the slurry volume that will be used in forming a bed of a desired height.

Figure 2:
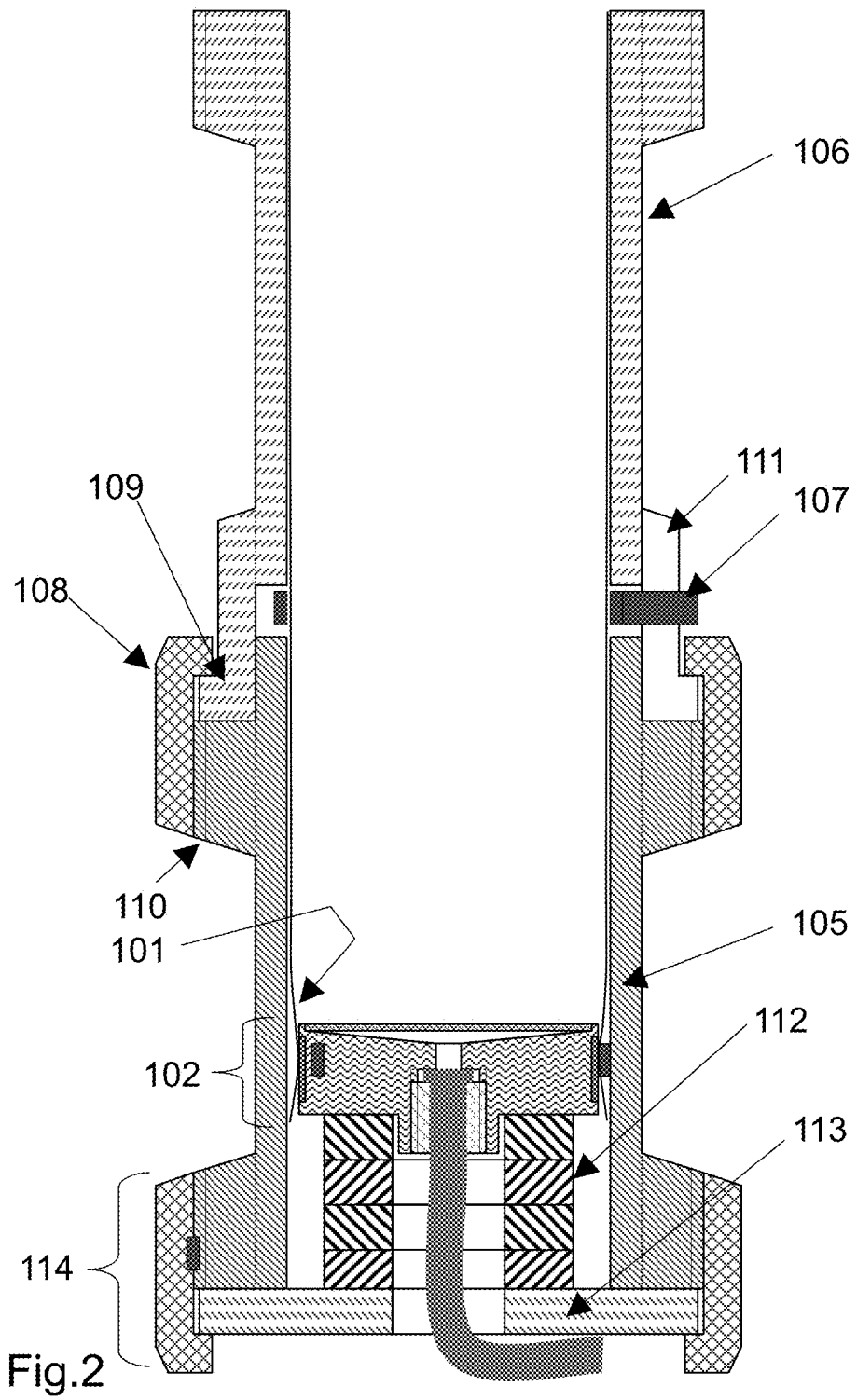
FIG. 2 is a cross section of the tubular liner and bottom plate of FIG. 1 positioned inside a column tube.

FIG. 2 depicts an assembly containing the following components:

Column tube 105. The column tube, also referred to herein as a column shell is rigid and supports the pressure inside the column. The diameter of the column tube 105 is identical to the diameter of the tubular plastic film 101 which is thereby fully supported by the column tube 105 and serves as a liner for the tube. If the tubular plastic film 101 is elastic and can expand, the column tube 105 can be slightly larger in diameter than the tubular film 101 to allow the tubular film to expand under internal pressure until the film 101 is in full contact with the tube 105. Such an expansion will ensure that the film 101 remains free of folds as it is being packed with media.

Tube extension 106. This extension, which is also referred to herein as a column shell extension, is mounted above and aligned with the column tube 105 and supports the pressure inside the column during the packing operation. Unlike the column tube 105, the tube extension 106 can be disconnected after the media packing is completed, as explained below and illustrated in a subsequent Figure. The diameter of the tube extension 106 can be equal to or slightly larger than that of the tubular plastic film 101 to offer the same benefits as those of the column tube 105.

Upper tie 107. At the junction between the tube extension 106 and the column tube 105 is a clearance for an upper tie 107, which can for example be a clamp, a collar, a wire, or any such device that can releasably secure the tubular film to a piston (explained below and depicted in a subsequent Figure). When engaged, the upper tie 107 has an inner diameter approximately equal to that of the tube extension 106, and provides a smooth continuation of the inner cylindrical surfaces of the tube extension 106 and the column tube 105. The tie 107 likewise surrounds the tubular plastic film 101 and supports the pressure inside the column during the packing operation. This upper tie 107 can be tightened by an external tool through an aperture between the tube extension 106 and the column tube 101. An alternative to such an aperture is a groove in the column tube 105, with an open slot for access of the tightening tool. A welding machine that welds the plastic film to the piston can be used in place of the tie 107.

Fixing Clamp 108. This clamp mechanically secures the tube extension 106 to the column tube 105 in a coaxial orientation with full alignment. The fixing clamp 108 also supports the pressure inside the column during the packing operation. The fixing clamp 108 in this embodiment is a nut that engages a shoulder 109 on the tube extension and is internally threaded to engage a threaded surface 110 on the column tube 105. As the fixing clamp 108 is being screwed to column tube 105, the fixing clamp 108 tightens the shoulder 109 of the tube extension 106 against the column tube 105. In the example shown in FIG. 2, the shoulder 109 contains a slot 111 on one right side to allow access to the upper tie 107. Any device that serves the function of a fixing clamp can be used, including for example a tri-clamp, a bolted flange, and tie rods. When packing is performed by an automated instrument, the tube extension 106 and column tube 105 can be held together by the components of the machine while leaving access to the upper tie 107 for the tightening tool.

Bed height adjustment 112. Optionally, the bottom plate 102 can be adjusted in height by a bed height adjustment system 112. This element allows an operator to adjust the bed height without changing the height of the column tube 105. In the embodiment shown, the bed height adjustment system 112 is represented as a stack of spacers, setting a controlled distance between the bottom plate 102 and a column support plate 113 at the bottom of the column. In the embodiment shown, the column support plate 113 is fixed to the column tube 105 by a three-part fixing clamp 114 similar to the fixing clamp 108 joining the tube extension 106 to the column tube 105. As in the fixing clamp 108, alternative means include a tri-clamp, a bolted flange, and tie rods. Still others will be apparent to those of skill in the art.

Figure 3:
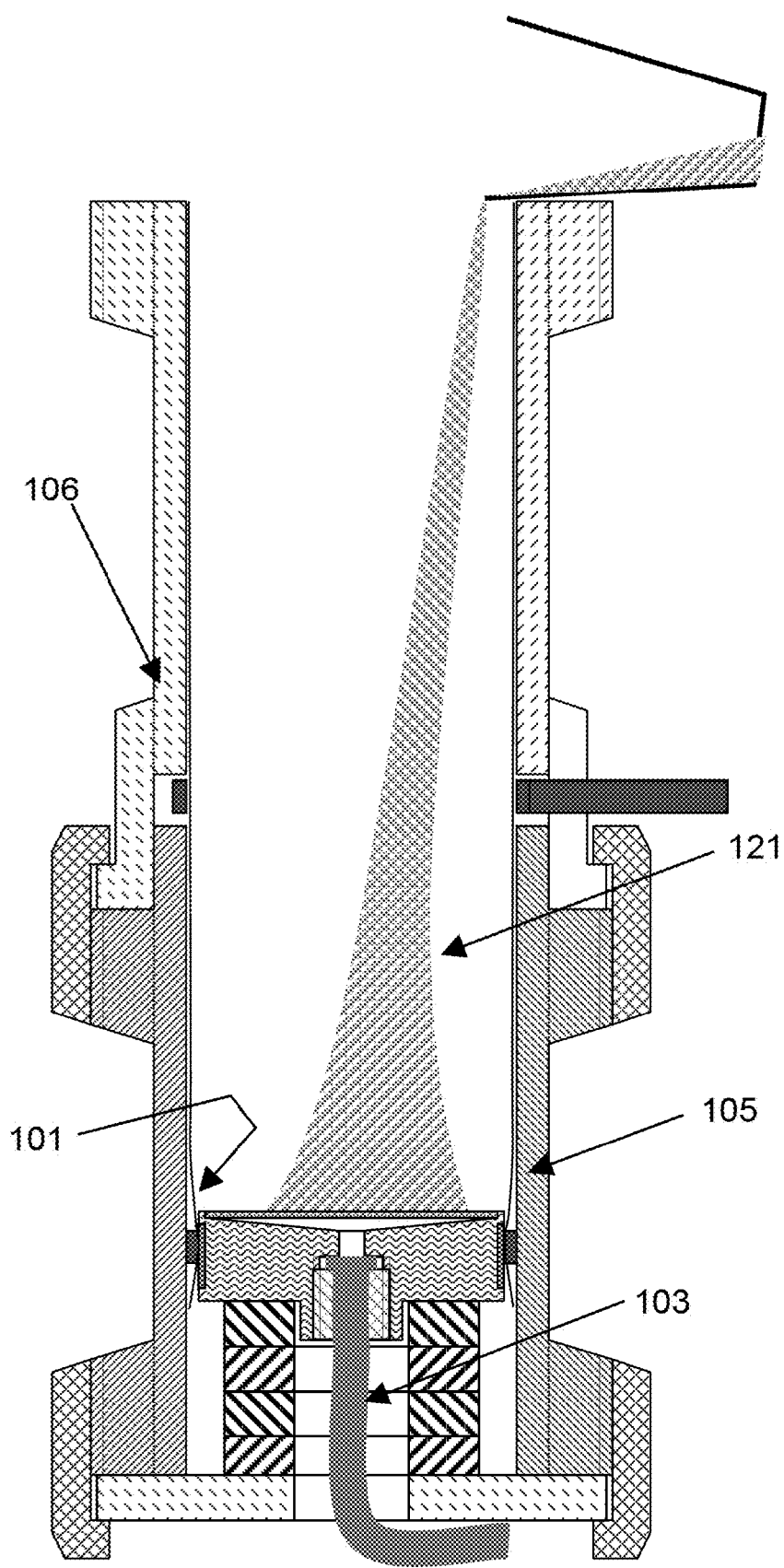
FIG. 3 is a cross section of the components of FIG. 2 shown with a separation medium being placed inside the liner.

FIG. 3 shows the start of the procedure for forming a packed bed in the column of the preceding Figures. A media slurry 121, i.e., a slurry of particles of the separation medium, is poured into the tubular plastic film 101 which is supported by the tube extension 106 attached to the column tube 105. The bottom process port 103 is closed at this stage, for example by a valve (not shown) on the column. The amount of media slurry that is poured is precisely selected such that when the slurry is packed down, the upper surface of the resulting packed bed will be just below the upper tie 107. Although shown as a suspension, the media can also be in the form of dry particles.

Figure 4:
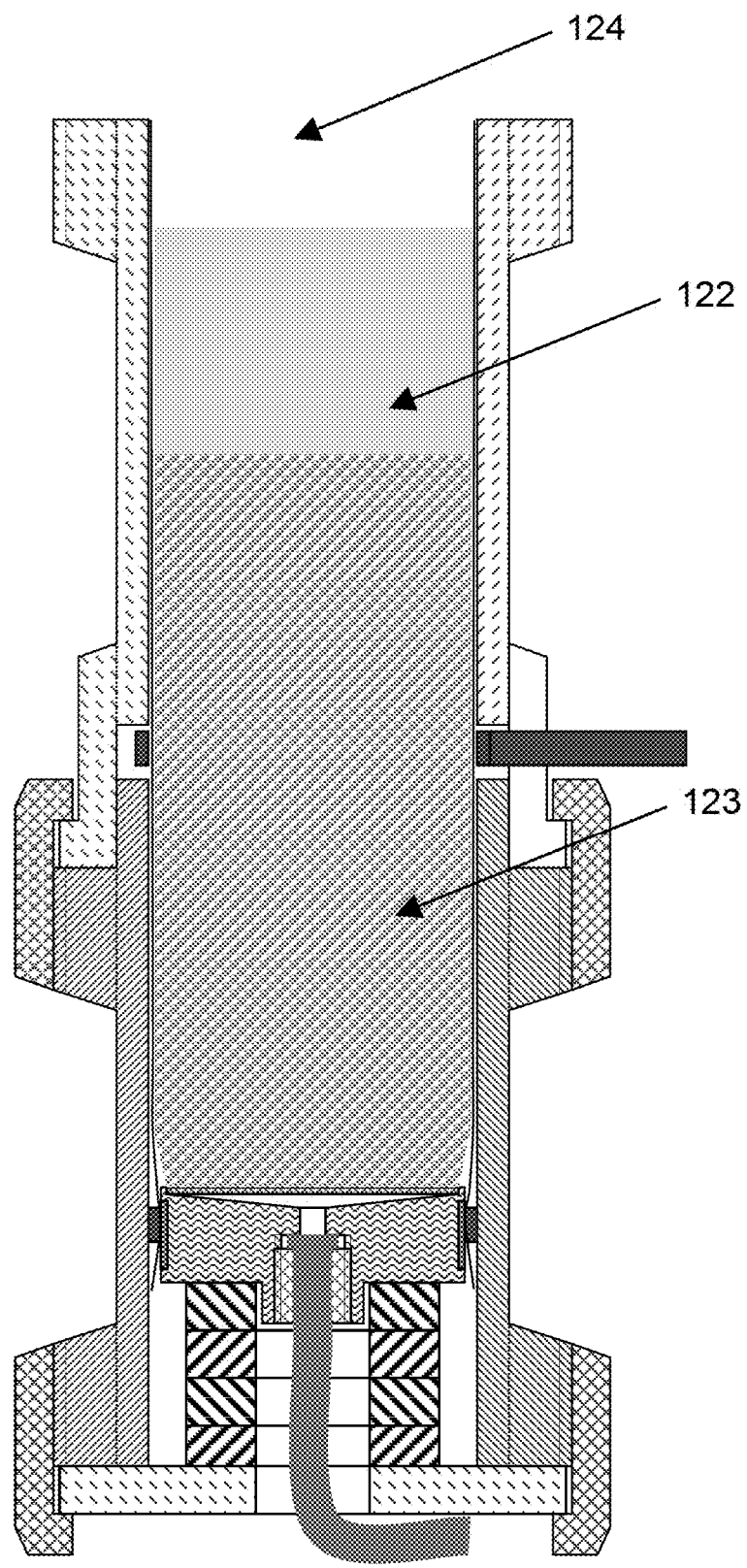
FIG. 4 is the same view as FIG. 3 after addition of the separation medium.

FIG. 4 shows a stage in which the media once poured has been allowed to settle for a period of time sufficient to leave a layer of clear supernatant 122 above the settled slurry 123. The starting amount of slurry should be such that enough space 124 is left in the tube extension 106 to accommodate the piston in the succeeding step.

Figure 5:
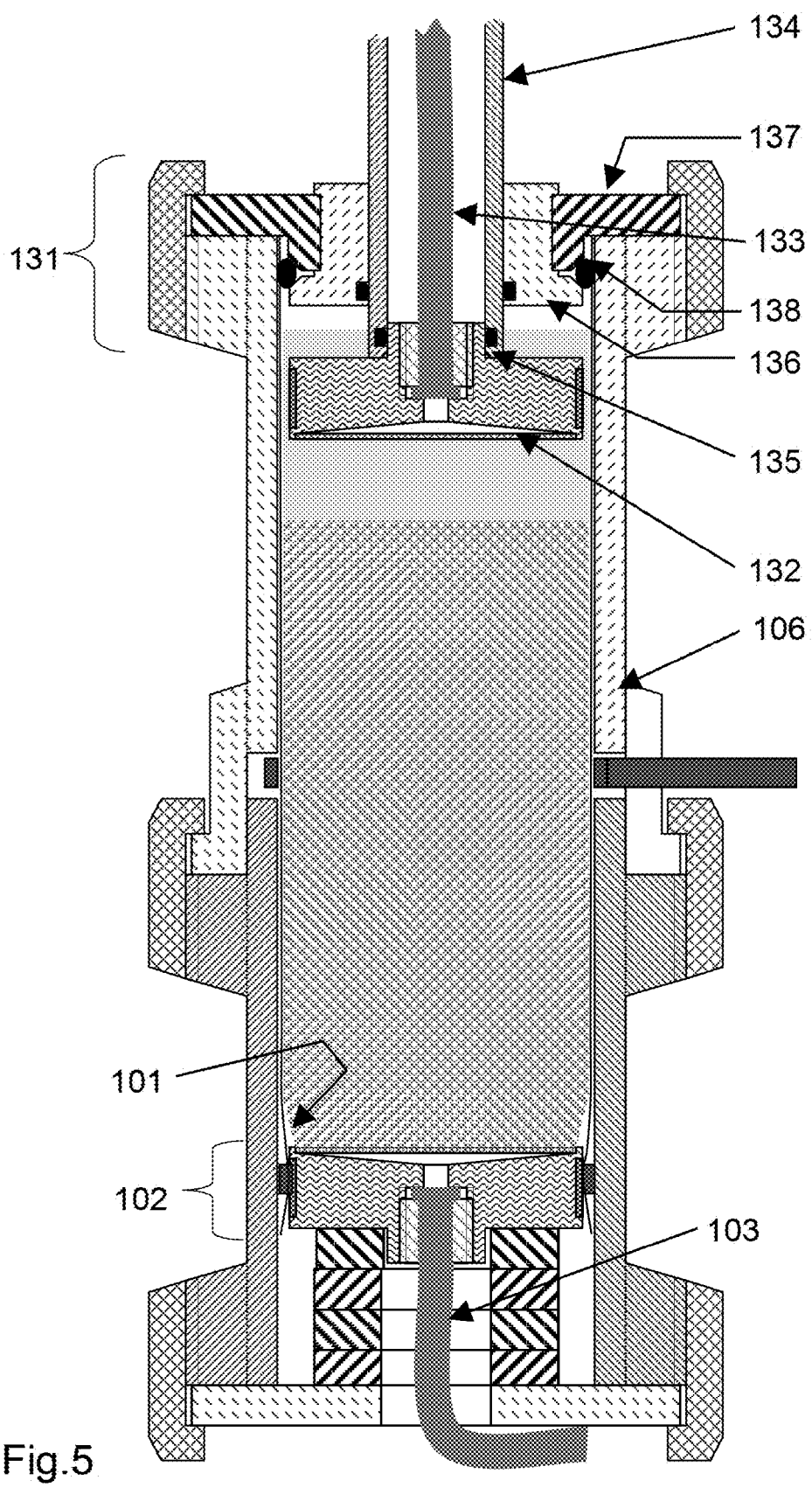
FIG. 5 is the same view as FIG. 4 with a piston added to compact the separation medium.

FIG. 5 depicts the column with a top assembly or cap 131 attached. The top assembly 131 includes a piston 132, a filter, and a top process port 133. These are similar to the corresponding features of the bottom plate 102, including a mobile phase distribution system within the piston. A piston shaft 134 supports the piston 132 and allows the piston to be lowered along the axis of the column tube 105. In the embodiment shown, the piston shaft 134 is a tube concentric with the column tube 105 and tube extension 106. An O-ring 135 between the piston shaft 134 and the piston 132 provides a water-tight seal and holds the piston 132 to the piston shaft 134 by friction, but a mechanical coupling can also be added if friction is not sufficient to hold the piston 132 under the piston shaft 134. The piston 132 fits inside the column tube and column tube extension as well as the tubular film in a manner permitting lowering of the piston within these parts.

The top assembly 131 holds the pressure inside the column during the packing operation. The top assembly 131 has a bore with an O-ring, scraper seal or other sealing means to allow the piston shaft 134 to slide in the bore along the column axis while ensuring a water-tight seal between the top assembly 131 and the piston shaft 134. The top assembly 131 also includes seal that hermetically seals top assembly 131 to the tubular plastic film 101. In the shown embodiment, the top assembly 131 is constructed in two parts: a bottom part 136 and a top part 137. The top part 137 has an outer thread that engages an internal thread in the bore in the center of the bottom part 136. Thus, by rotating the bottom part 136 relative to the top part 137, the distance between the two parts can be varied. On their outer edges, the bottom part 136 and top part 137 have two opposing chamfers which accommodate an O-ring 138. When the bottom part 136 and top part 137 approach each other, the opposing chamfers do likewise and push the O-ring 138 radially against the tubular plastic film 101 which then tightens against the bore of the tube extension 106. The top assembly 131 can be tightened over the tubular plastic film 101 to ensure that the pressure inside the column can be held. If the film 101 is sufficiently elastic, an alternative solution to assembly 131 is possible as further depicted on FIG. 18.

The top assembly 131 is secured to the tube extension 106 in the following manner. Once the slurry has settled, a layer of supernatant 122 remains, and the piston is immersed in the supernatant. If the slurry has not been allowed to settle, the piston must be placed in the empty space 124 above the slurry. Media should not travel to the region above the piston during this process. Once the piston 132 is in place, the top assembly 131 is tightened against the tubular plastic film 101. With the top assembly 131 secured, the inner side of the tubular plastic film is sealed against the bottom plate 102 and also against the top assembly 131. At this stage the piston 132 is not tightly secured to the tubular plastic film 101, and liquid can freely move between the region below the piston and the region above the piston. This avoids the need for a dynamic seal, i.e., a seal between a moving part as the piston 132 and a static part as the liner 101. Shear stress on the plastic film 101 is thus avoided, as is the need for an expensive column tube with a calibrated and smooth bore. A further benefit is that neither the tube extension 106 nor the column tube 105 are required to be made of food-grade or drug-grade material. This reduces the cost of the column even further.

Figure 6:
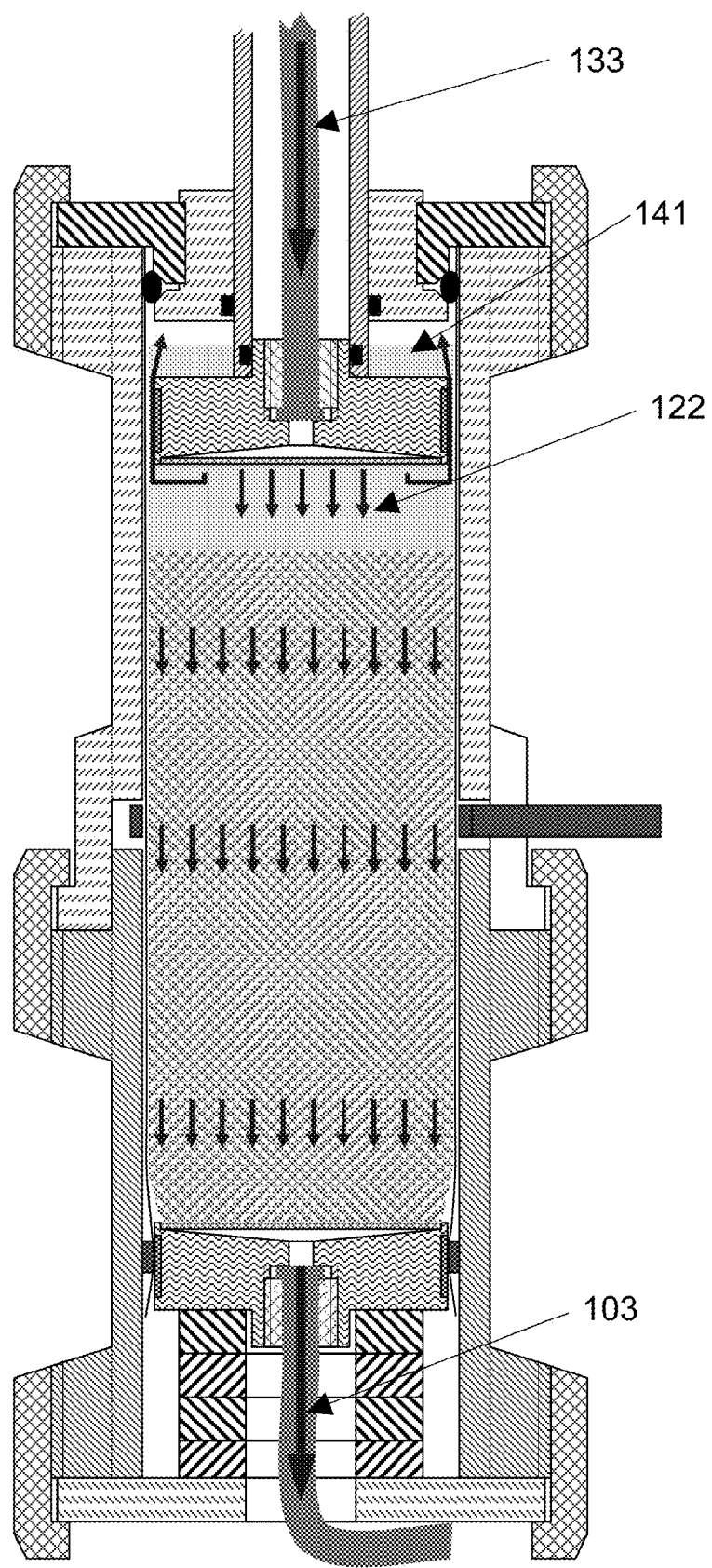
FIG. 6 is the same view as FIG. 5, showing the direction of movement of the piston.

FIG. 6 illustrates the start of the packing operation. As further shown on FIGS. 15 to 18, the optimal packing performance is obtained with a combination of percussion and flow packing The percussion system is not shown on FIGS. 6 and 7 which only represents the "flow packing," which consists of circulating the mobile phase, i.e., the packing buffer, between the top process port 133 and the bottom process port 103 under controlled flow speed, controlled pressure, or both.

During packing operation, as further described with FIGS. 15 to 18, the slurry bed begins to consolidate. This creates flow resistance and thus increases both the pressure drop across the bed and the hydraulic pressure inside the column. Since the piston 132 is not tight against the column tube 105, the pressure under the piston and the pressure above the piston equilibrate to each other, and as the pressure drops across the bed increases, some liquid below the piston will move above the piston until the pressure equalizes. Since the top chamber is sealed on the upper side, however, most of the mobile phase circulates through the packed bed to reach the bottom process port where it can escape the column.

The upper chamber, i.e., the region 141 above the piston 132, serves as an air trap. If air is introduced into the column with the mobile phase, the bubbles move to the outer side of the piston where they can rise within the upper chamber through the clearance between the piston 132 and the tubular film 101. This leaves the bed free of air as the bed is being formed, a condition that is of value towards obtaining a homogeneous and compact bed as needed for the purification.

Figure 7:
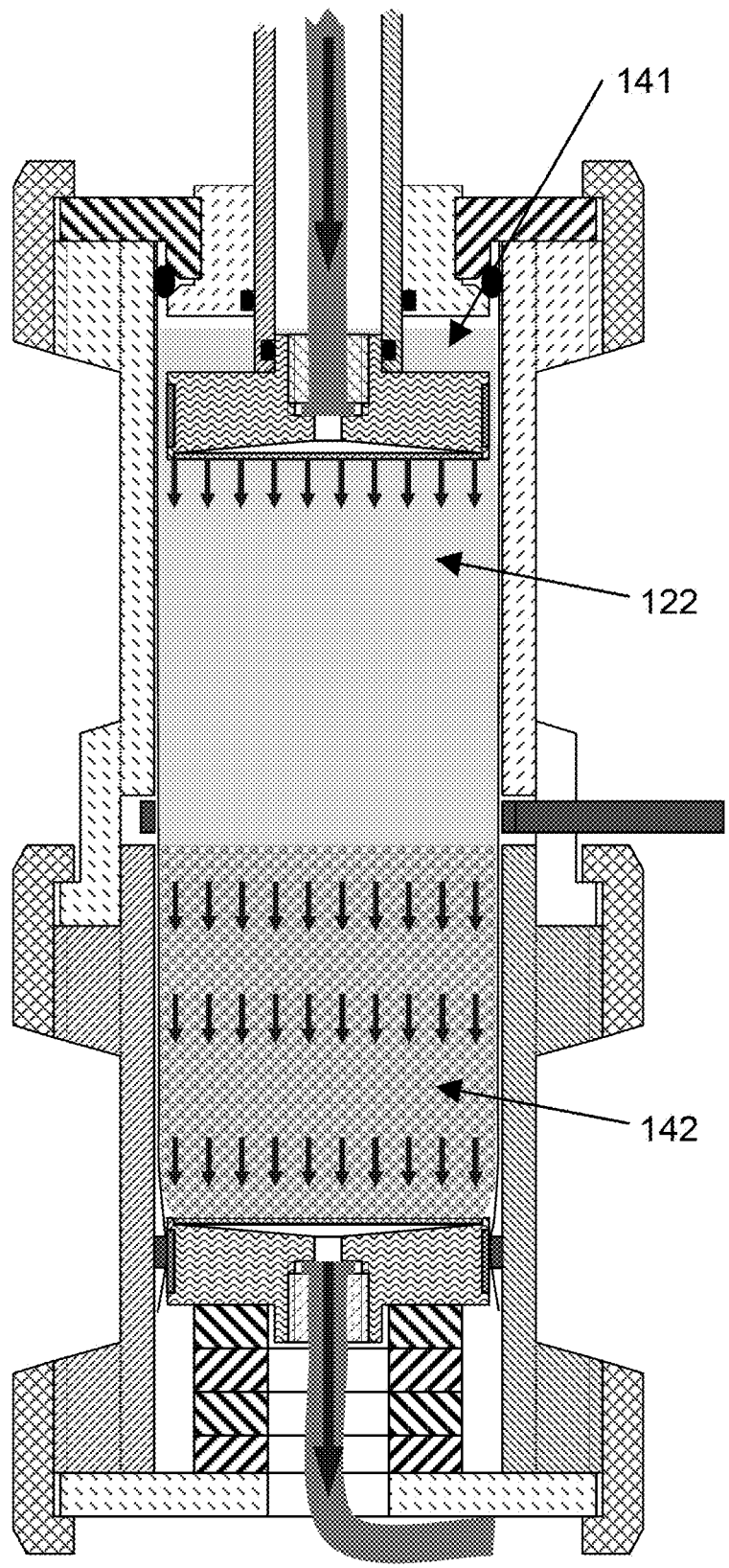
FIG. 7 is the same view as FIGS. 5 and 6 after the bed of separation medium has been fully packed.

FIG. 7 depicts a consolidated (packed) bed 142. When the bed is consolidated, the pressure drop across the bed is stabilized. Since the pressure is now constant in the column and is the same both above and below the column, the flow rate of the mobile phase exiting the column is equal to the flow rate of the mobile phase entering the column through the piston.

Figure 8:
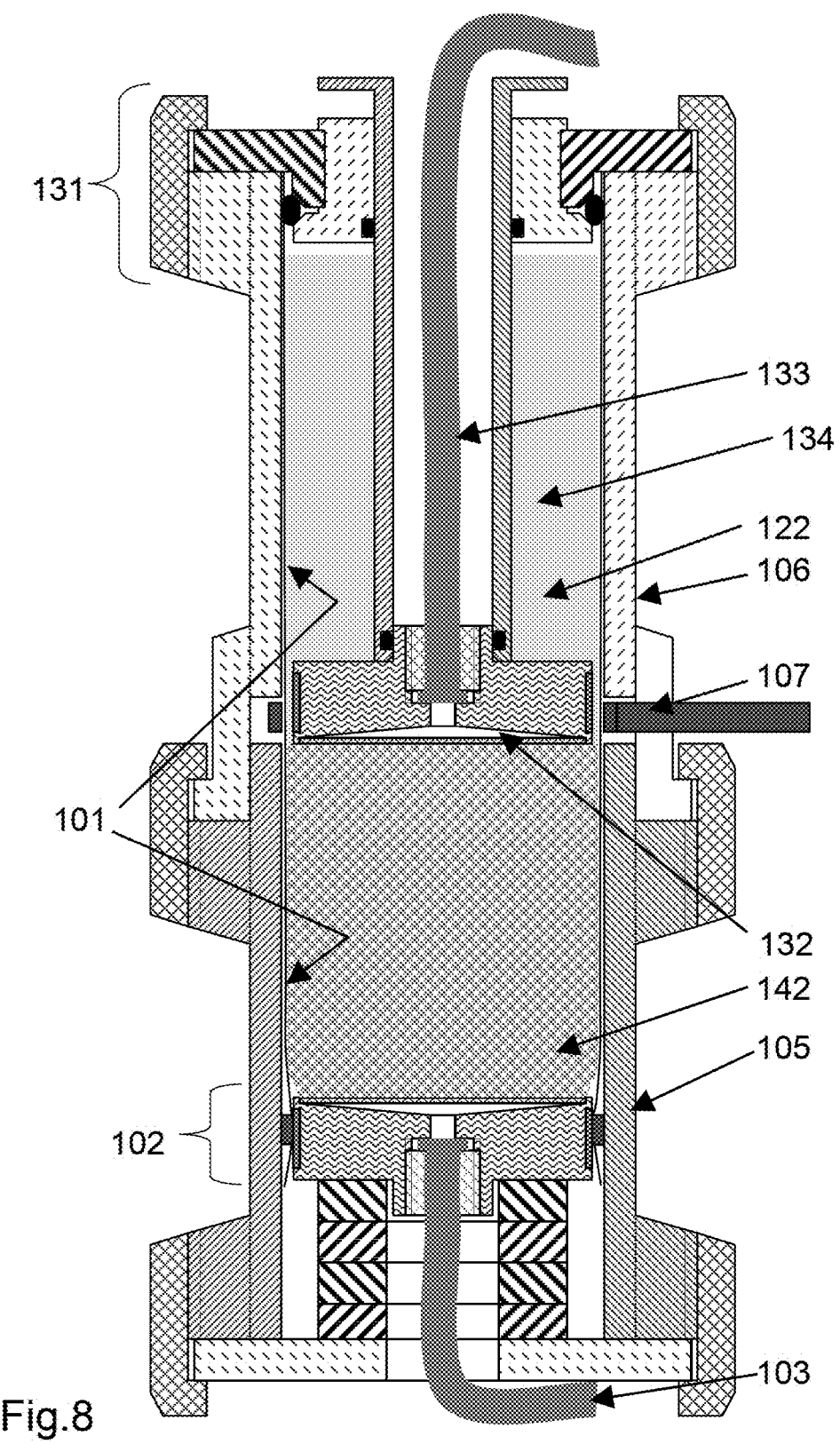
FIG. 8 is the same view as FIG. 7 after the piston is lowered against the bed.

FIG. 8 depicts removal of the supernatant. Once the bed 142 is fully consolidated, the piston 132 is moved down in the supernatant until the piston 132 meets the bed 142. As noted above, the quantity of media originally introduced in the column is selected to cause the height where the piston 132 meets the consolidated bed 142 to be level with the position where tubular film 101 can be tightened against the piston 132 by the upper tie 107.

As the piston 132 is being lowered within the column, the internal volume between the column tube 105, the tube extension 106, the top assembly 131 and the bottom plate 102 is reduced by the volume consumed by the length of the piston shaft 134 that is inside the column. Since liquid is almost incompressible, the top process port 133, bottom process port 103, or both should be left open so that the volume consumed by the piston shaft 134 is compensated by an equal volume of mobile phase leaving the column by either port.

Figure 9:
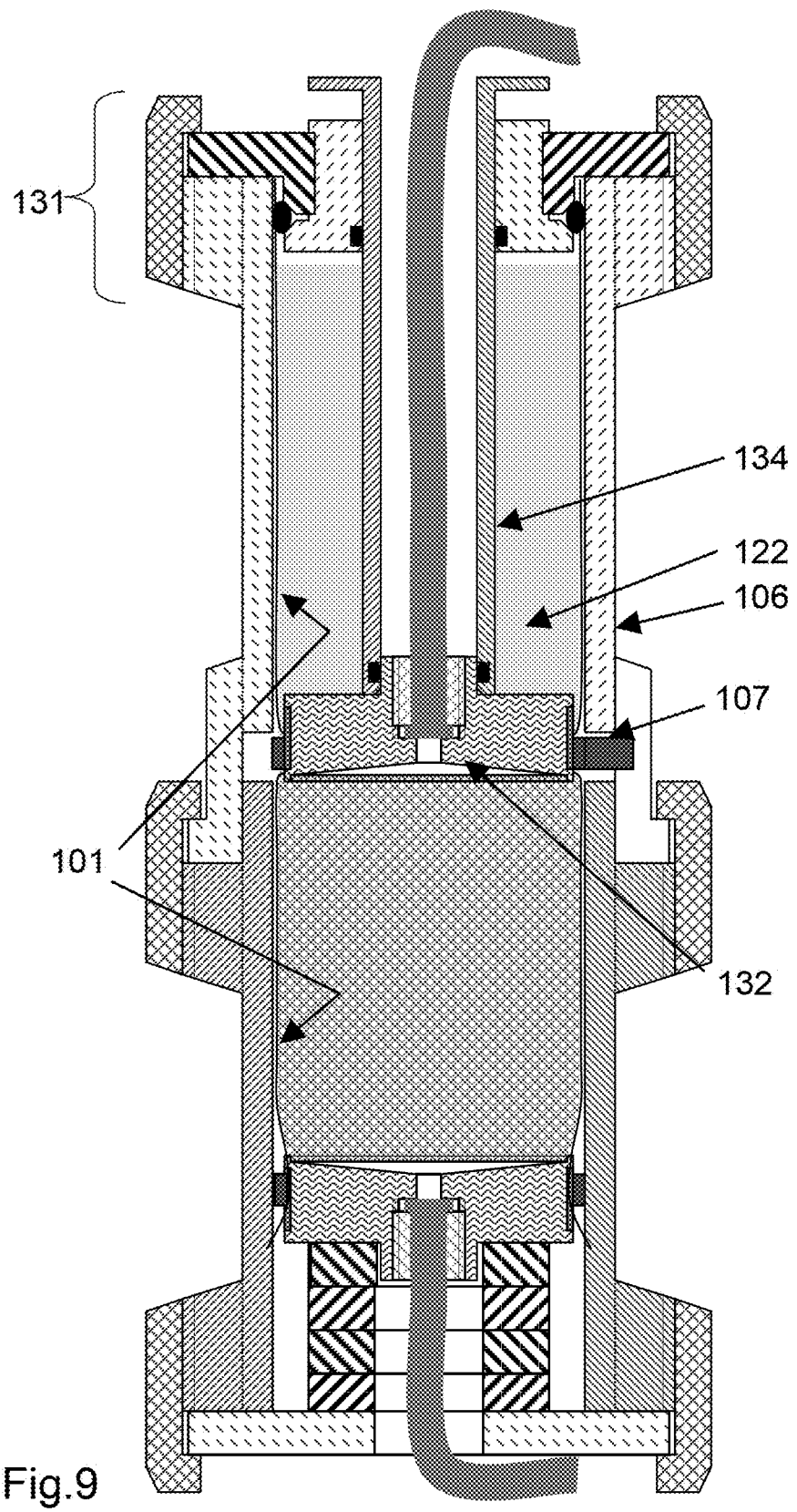
FIG. 9 is the same view as FIG. 8, showing the line sealed over the piston.
Figure 10:
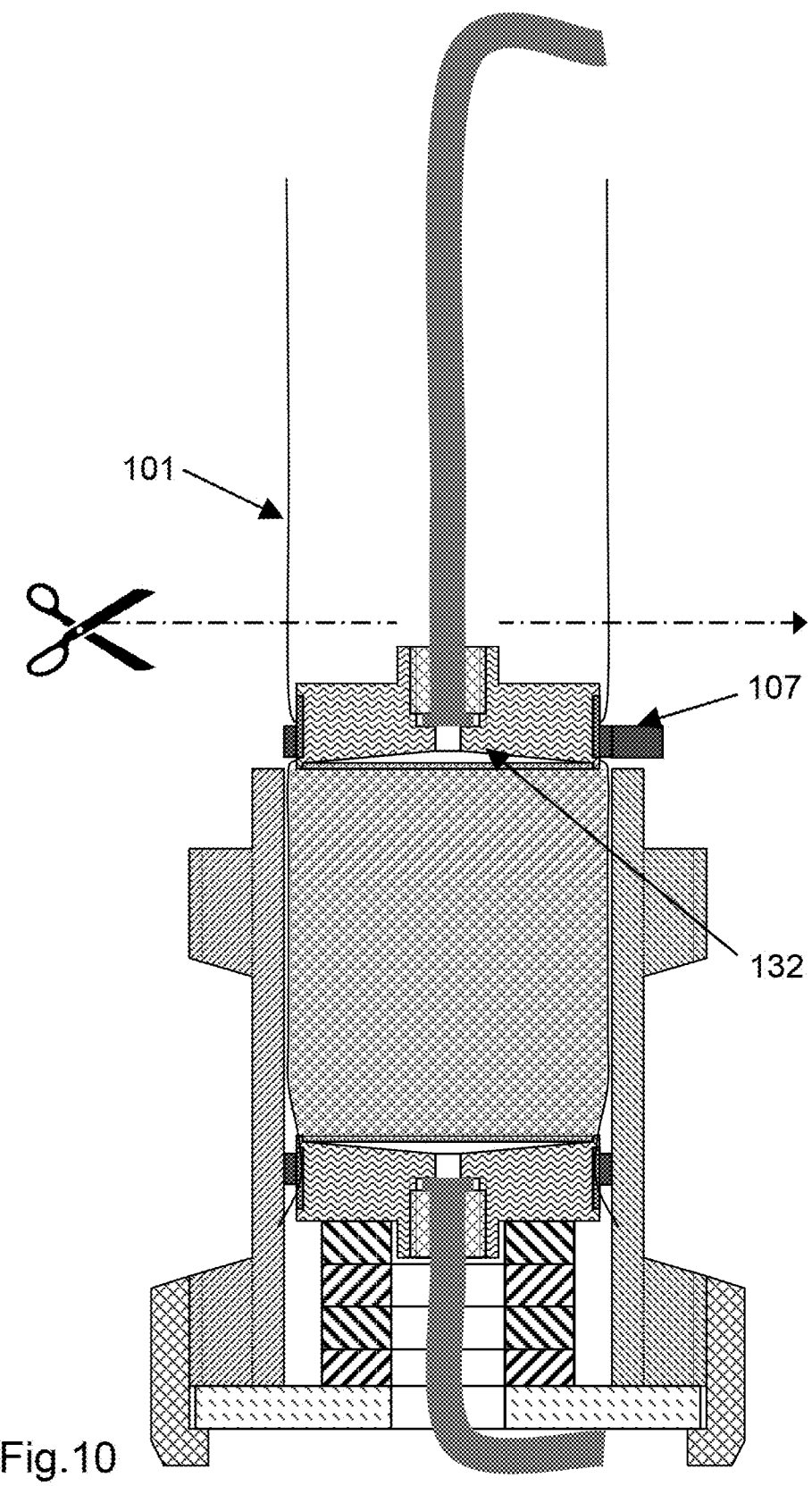
FIG. 10 is the same view as the preceding Figures, showing removal of certain parts of the structure following the sealing of the liner.

FIGS. 9 and 10 depict the sealing of the piston 132. The upper tie 107 is first tightened to form a hermetic seal between the tubular plastic film 101 and the piston 132, as shown in FIG. 9. Once the seal is formed, the top assembly 131, the tube extension 106, and the supernatant 122 above the piston 132 can be removed to achieve the condition shown in FIG. 10. Removal of the top assembly 131, the tube extension 106, and the supernatant 122 can be achieved by first disengaging the piston shaft 134 from the piston 132, then emptying the supernatant 122 through an aperture inside the piston shaft. The seal between the top assembly 131 and the tubular plastic film 101 is then broken. The top assembly 131, piston shaft 134 and the tube extension 106 are then removed.

If the separation medium has been compressed in the column during packing, as is typical with soft or semi-rigid media, the medium usually exerts a force against the piston, the magnitude of the force being related to the Young's modulus of the medium. If the tubular plastic film 101 cannot hold this strength on its own and tends to expand and reduce the density or uniformity of the bed, an external device can be used to maintain the position of the piston. The tool used to tighten the upper tie 107 is an example of one such device.

If desired, the section of tubular plastic film extending above the piston can be cut and removed, since it serves no function in the further operation of the column, other than to preserve the option of resuspending the medium in the tubular plastic film at a later point in time. Resuspension can be accomplished by remounting the top assembly 131 and detaching the upper tie 107, followed by proceeding with an inverted sequence from FIG. 9 back toward FIG. 1.

Figure 11:
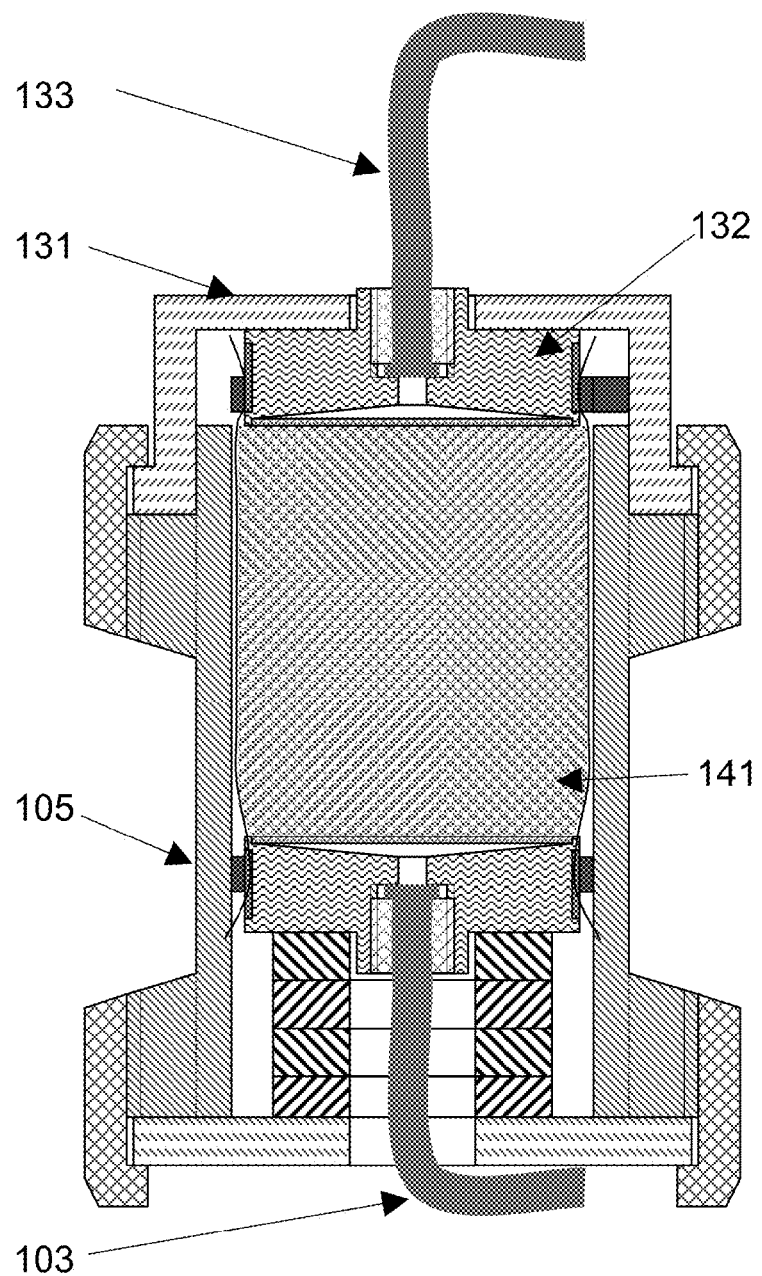
FIG. 11 is the same view as the preceding Figures, showing a subsequent stage in which a cap is placed over the top of the column.

FIG. 11 depicts the configuration of the column for purification. A cap 131 is secured to the top of the column tube 105. The cap 131 serves to hold the hydraulic pressure in the column during the use of the column, i.e., during sanitization, purification, etc. The cap 131 also maintains the mechanical pressure of the bed 142 against the piston 132, as described above. Still further, the cap 131 can be used to further compress the bed by pushing down the piston, while either the bottom process port 103 or the top process port 133 is left open to allow removal of an equal volume of mobile phase.

The configuration of the packed column as shown in FIG. 11 offers multiple advantages:

(1) The overall size of the column is minimal, since the tube extension 106 used in the column preparation has been removed.

(2) The number of parts in contact with product is minimal: they include only the piston 132, the bottom plate 102, the process ports 103, 133, and the inner surface of the tubular plastic film 101. Since food-grade and drug-grade materials are expensive, minimizing their use lowers the cost of the column. This also allows the column to be used as a "disposable" column.

(3) Most of the parts of the column, i.e., the column tube 105, the support plate 113, the tube extension 106, and the top assembly 131, are for mechanical support only. There is no requirement that they be constructed of materials compatible with drugs or food, or materials compatible with the process solutions. Since they do not come in contact with the product, they can be recycled for other applications without risk of cross contamination.

(4) In preparative chromatography columns in which the piston is smaller than the column tube, the mobile phase distribution system often fails to extend the mobile phase to the outer parts of the column. Poor irrigation of these outer parts can raise sanitation concerns. With the present invention, the tubular plastic film 101 is tight around the piston 132, and the column section inside the tubular plastic film under the piston is very close to the piston itself, thereby mitigating concerns regarding distribution and sanitation.

(5) The column can withstand high hydraulic pressures, and its ability to do so is limited only by the dimensions of its mechanical components. The tubular plastic film is supported in every direction and serves as a liner which requires no mechanical resistance, except at the sections where the plastic film 101 is tightened against the bottom plate 102 or the piston 132. Sections of the tubular plastic film that are not supported may expand in response to high pressure inside the column, leading to a risk of rupture, but this risk can be mitigated by filling the space between the cap top assembly 131 and the piston 132 and the space between the bottom plate 102 and the support plate 113 with an external liquid. This external liquid will not be in contact with column interior, and yet it will hold the film where it is not supported with mechanical parts.

(6) The tubular plastic film 101 can be thin and transparent, which facilitates temperature sensing and pressure sensing, as well as the detection of optical, ultrasonic or other signals through the film. The film thus avoids the need for costly instruments designed for food and drug contact and the need for materials that are compatible with the process solutions. The film also eliminates concerns of cross-contamination between runs. Instrumentation for sensing and detection can be placed in direct contact with the film, for example by inserting such instrumentation in the column tube, or placed in contact with external fluid as described above.

(7) The use of a thin, transparent tubular plastic film can also be beneficial for heat exchange, whether by electrical resistance heating on the column tube or by circulation of liquid outside the tubular plastic film. Fine grooves can be formed in the column tube 105 to provide channels in which cooling or heating liquid can circulate without direct contact with the process liquid inside the column.

(8) The column tube can be made of an opaque material, such as plastic, steel or stainless steel. A slot can be included in the column wall along the length of the column to allow observation of the bed. The optimal slot is one that is wide enough for observation through it but narrow enough to avoid protrusion of the tubular plastic film through the slot under hydraulic pressure. The slot can thus serve as a low-cost sight glass.

(9) A tubular plastic film with high mechanical resistance, such as one made of plastic film coextruded with a textile structure, can be used without the top assembly 131 and the support plate 113 or even without the column tube 105.

(10) The features described above are readily adapted in preparing a chromatography cartridge as depicted in FIG. 12. This cartridge contains a piston 132, bottom plate 102, a top process port 133, a bottom process port 103, ties (such as rings 104, 107), the tubular plastic film 101, a low-cost outer tube 168, and a clamp 169 for maintaining the desired distance between the piston 132 and the bottom plate 102. The low cost tube 168 fits inside the wider column tube 105 depicted in the preceding Figures.

Dismantling of the column of FIGS. 1 through 11 is depicted in FIG. 13. The top assembly 131 is opened and parts including the bottom plate 102, the tubular plastic film 101, the lower and upper ties 104, 107, and the piston 132 are lifted from the column tube 105. As an alternative, the upper tie 107 can be loosened and the piston 132 removed, to permit removal of the packed media from above, and the bottom clamp 114 then dismounted to allow the bottom plate 102 and tubular plastic film 101 to be removed. The column tube 105, bottom clamp 114, bed height adjustment system 112, top assembly 131, bottom clamp 114, and other parts can then be re-used.

FIG. 15 presents the principle of a further packing method using percussive tapping to the base of the column, thereby assisting uniform packing In this picture, the column is just depicted by its top plate 170, bottom plate 102 and bed of media 172. It also shows how flow packing can be performed, by using a pump 174 optionally followed with an air trap 179 for ensuring that the mobile phase will be free from gas.

The flow of mobile phase figured with arrows 173 exerts downward strength against the media particles which adds to the gravity force. This forces the media particles to settle in a stable manner against lower particles or column walls. The higher this downward strength, the faster the particle settles and the stronger is the strength exerted by this particle against lower layers, inducing some local rearrangement until equilibrium is met. Flow packing prevents large particles from settling before small particles. If the particles were instead allowed to settle by gravity, the big particles would settle first and collect at the bottom of the column while the small particles settle more slowly, causing them to become concentrated at the top of the column. Faster settling also reduces the time where percussion has to be maintained and hence reduce the risk of damage of the particles. This downward strength has to be maintained during all the time percussion is performed.

The percussion table 175 can contain a mobile mass 175$a$, referred to here as a hammer, actuated vertically by an actuator 175$b$ fixed on the floor. This hammer 175$a$ is periodically projected against a plate 175$d$, to which its energy is transmitted. In the embodiment depicted in the FIGS. 15 to 18, the plate 175$d$ is linked to the ground by elastic blocks 175$c$ with low stiffness at low frequency so as to minimize the shock absorption. These elastic blocks 175$c$ can be replaced with springs. Shocks can also be less absorbed by implementation of cylindric joints in place of 175$c$ which just guide the plate 175$d$ without constraint on the vertical movement. With a given period, the hammer 175$a$ exerts shock to the plate 175$d$ which lifts it up slightly (configuration on the right). Under the gravity force of the table 175$d$ and the stiffness of the elastic blocks, the percussion plate comes back to its lower position (configuration on the left) resulting with another shock.

In some embodiments, percussion can be provided with a rotary hammer drill, with rotation inhibited.

The percussion provides energy and upward acceleration to the particles to move from equilibrium of higher energy to equilibrium of lower energy (ie: more stable). The crossing from one to the other requires energy to leave the first equilibrium, for instance, to climb over a neighbor particle or force it to move sideward or overcome a static friction.

This percussion differs in many manners from sinusoidal vibration, performed by the rotation of an unbalanced mass or vertical back and forth movement of a mass with an actuator fixed on the vibrating table. In the methods described herein, the frequency of the percussion is low (for example, from about 0.2 to about 100 Hz with an amplitude less than about 5 mm, while sinusoidal vibration exerts usually above about 50 Hz. In some embodiments, the percussion involves very high acceleration due to the hurtling of the mass of the hammer while acceleration is limited on sinusoidal vibration. In some embodiments, the percussion only acts along vertical direction, in the longitudinal axis of the column, while sinusoidal vibrator is usually multi directional in a plane, or unidirectional if combined by an opposing pair. In some embodiments, the percussion targets essentially particle rearrangement in the bed, while with higher frequency sinusoidal vibration, it often targets friction reduction (wall effect, etc.).

The strengths of the two actions, percussion and downward strengths, add themselves along the vertical axis. Percussion is discontinuous, while vertical strengths (gravity+flow circulation) are continuous. Maximum magnitude of strength of percussion is generally higher than downwards strength. Hence the resultant strength is always vertical, sometimes in upward direction, during the upward percussion impact where its magnitude is higher than downward strength, sometimes in downward direction, during the downward percussion impact added with downward strength or when no percussion takes place. The mean value of the resultant strength is positive in downward direction for allowing the media packing.

The FIG. 16 depicts one embodiment of the column assembly with the tube extension, similar to FIG. 5, mounted on the percussion table. The percussion table is shown in two configurations: in low position on the left when the hammer 175$a$ is at rest, in high position on the right when 175$d$ is hurt by the hammer 175$a$. In this embodiment the whole column assembly is submitted to the percussion.

The FIG. 17 depicts one embodiment alternative to the one of FIG. 16, where the top parts comprising the top assembly 131, the tube extension 106, the piston 132 and the piston shaft 134 are isolated from the bottom parts of the column and from the percussion table 175. These top parts are mounted on an independent frame 180 attached to the tube extension 106. The liner 101, made of soft material, allows for uncoupling of the top parts from percussion, while keeping the water tightness inside the column between the bottom parts submitted to percussion and top parts uncoupled from percussion. Thus, in some embodiments, the top parts are not submitted to the mechanical strength of the percussion with consequent material fatigue over time. This also reduces the weight over the percussion table 175, hence its inertia. The inertia being reduced, the acceleration is increased, considering Newton's law.

The FIG. 18 depicts one embodiment alternative to the one on FIG. 16 and FIG. 17 for the top assembly 131. This assumes that the liner 101 is sufficiently soft to be tucked over a neck 184 fitted above the tube extension 106. Once the liner 101 is tucked over, the top part 137 is mounted and tight against the neck 184, by a nut 181, or a clamp or a bolted flange as for 108 in FIG. 2. When tightened, the liner 101 is pinched water tight. This solution for sealing the liner in the column can be easily implemented on every embodiments of this invention.

Another optional change compared to the former embodiments also appears on FIG. 18. The top plate 137 incorporates a slurry injection port 182. This slurry injection port 182 encloses a valve which can close the aperture during the packing operation and is hence designed to resist hydraulic pressure during this operation. The hollow shape of 137 allows for positioning the piston 132 above the aperture of the slurry port so as the slurry can be injected under the piston 132. The dotted line 132s shows the piston 132 when positioned in the upper position above the slurry port. By injecting the media through 182 while mobile phase is also injected through the piston 132, the slurry is carried in the flow and quickly settled in the bottom of the column. This configuration ensures that media particles don't travel to the region above the piston. It also allows adjusting the level of media in the column if the upper surface of the packed bed does not reach the upper tie 107, for instance due to bad dosing of media. It also allows direct "dosing" of the media in the column during bed construction. A possible method can be to fill the column with packing buffer, with piston 132 positioned above the slurry port aperture, and continuously circulate packing buffer from top process port 133 to bottom process port 103 while injecting media through 182 until the upper surface of the resulting packed bed will be just below the upper tie 107. To avoid that the side positioning of 182 induces an uneven distribution of the media in the column, several slurry injection ports 182 can be implemented, or the media can eventually be resuspended in place, after this initial filling, by upflow circulation of packing buffer from bottom process port 103 to top process port 133, or by air sparging through the bottom process port 103. The packing operation with combination of percussion and flow packing can then be repeated with the slurry injection port shut off.

Figure 21:
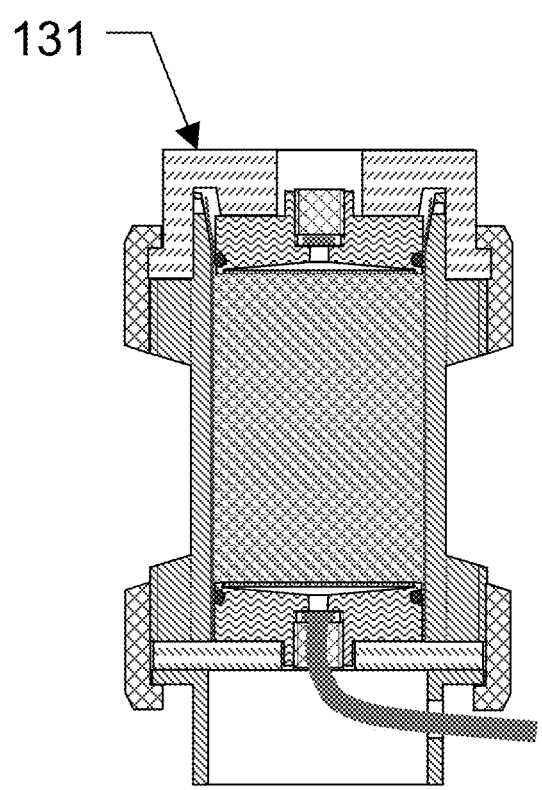
FIG. 21 is the same view as the FIG. 27, showing a subsequent stage in which a cap is placed over the top of the column.

The FIGS. 19 to 21 depict an alternative design of the column, especially for the sealing of the liner 101 with the piston 132 and eventually also with the bottom plate 102, but the principle of the packing method stays unchanged. In this embodiment, the sealing between the liner and the piston 132, and eventually of the bottom plate 102 as shown on FIG. 19, is not obtained by external tie such as 104 and 107 in former embodiments, but by a seal 183 that can be for example an O-ring or any other seal including but not limited to a lobe joint or a scraper seal. In this case, the hollow of 105 is precisely dimensioned, at least where parts 132 and 102 have to sit, so as the seal 183 makes a sealing between the liner 101 and the piston 132 when engaged at the top of 105 or between the liner 101 and the bottom plate 102 when engaged in the bottom of 105.

As explained in formers section describing FIGS. 5 & 6, the piston 132 does not fit tightly with the film 101 when positioned in the tube extension 106. With the embodiment of FIG. 19, this can be obtained by designing the hollow of 106 with a larger diameter than in tube 105 so that the seal 183 does not fit tightly between the piston 132 and the liner 101 in the tube extension 106. This supposes that the liner is soft enough to expands to the inner diameter of 106 under hydraulic pressure. The same packing method as described in FIGS. 5 to 7 can be applied. When the bed is consolidated as represented on the FIG. 19, the piston 132 is lowered and engaged in the tube 105. This generates a chamfer (i.e. an edge), adapting the inner diameter from the inner diameter of 106 on the upper edge of 105 to the diameter where the seal 183 can fit tightly between the piston 132 and the liner 101. This chamfer hence guides the piston and progressively compresses the seal 183 until the piston 132 meets the bed and gets sealed with 101 as shown on FIG. 20.

At this position, the piston 132 must be held in place to allow the dismounting of the piston shaft 134, the top assembly 131 and the tube extension 106. The holding of the piston has to withstand the strength exerted by the media, e.g., as discussed above. FIG. 20 depicts two possible solutions with 185 and 186 that can be optionally be combined for holding the piston. Other solutions that can hold the piston in place are also possible. Part 186 is one or several needles guided through an aperture in 105. When introduced in the column, this needle(s) 186 pierces the liner and holds the piston as a stop piece to counter the upper strength applied by the media against the piston 132. This needle(s) 186 can be connected to a vessel and hence can remove the supernatant above the piston 132 before the dismounting of the upper parts (106, 134, 101). If for any reason, the liner 101 must not be pierced (for instance, if the tube extension and liner are left for allowing multiple packing and unpacking), one or several pins 185 can be fitted in the same way than 186 with the difference that the pin(s) do not pierce the liner but are simply pushed inside the column as shown on the magnified view FIG. 20a. The design of the solution ensures that 185 and/or 186 can be maintained on 105 without preventing the dismounting of the upper parts 106, 134 and 101.

Once these upper parts have been removed, the cap 131 can be installed as depicted on FIG. 21. The pin(s) 185 or needle(s) 186 can be dismounted after the cap is installed, or left in position. They can also be removed before the cap 131 is installed, if an external force holds the piston in place between the moment the needle(s) 185 or pin(s) 186 are removed and the moment where cap 131 is installed.

One interesting extension of the embodiment described in FIGS. 19 and 20 is that this solution can be easily adapted to a configuration without the liner 101. In this case, the piston 132 and the bottom plate 102 are directly in contact with the tube 105. In this aspect, the tube extension 106 is mounted in a water tight fashion on the top of the column tube 105 by a seal. In some aspects, the tube extension 106 and the tube 105 can be designed as a single assembly in one piece or made of parts welded or assembled together. In this aspect, the parts 105 and 106, being in contact with the product, are ideally made of food-grade or drug-grade material.

This invention is useful in plug-flow chromatography applications of any scale, from small diameters for laboratory usage up to a large industrial scale. The invention can also be used with any kind of separation media, including matrices based on natural polymers, organic polymers, and inorganic materials such as hydroxyapatite, silica, $TiO_2$, and diatomaceous earth.

The invention is also readily adapted to expanded bed applications, by using the upper assembly and the tube extension during the period where bed is being expanded. The invention is readily adapted to packing techniques other than that described above. The invention can also be practiced by stacking columns as shown in FIG. 14 while using a single tubular plastic film, by repeating the sequence of FIGS. 2 through 9 multiple times. When packed with the same separation medium, the stacked columns can save floor space. With stacked columns, the mobile phase is distributed equally between the different inlet ports of the columns and collected from the different outlets of the column at the same time, achieving a result equivalent to that obtainable with a larger column. When packed with different kinds of media, the stacked columns can be used for the different purification steps. Since each section of the column will have its dedicated inlet and outlet process ports, the column sections can also be used with different buffers and different instruments, as independent columns.

Figure 22:
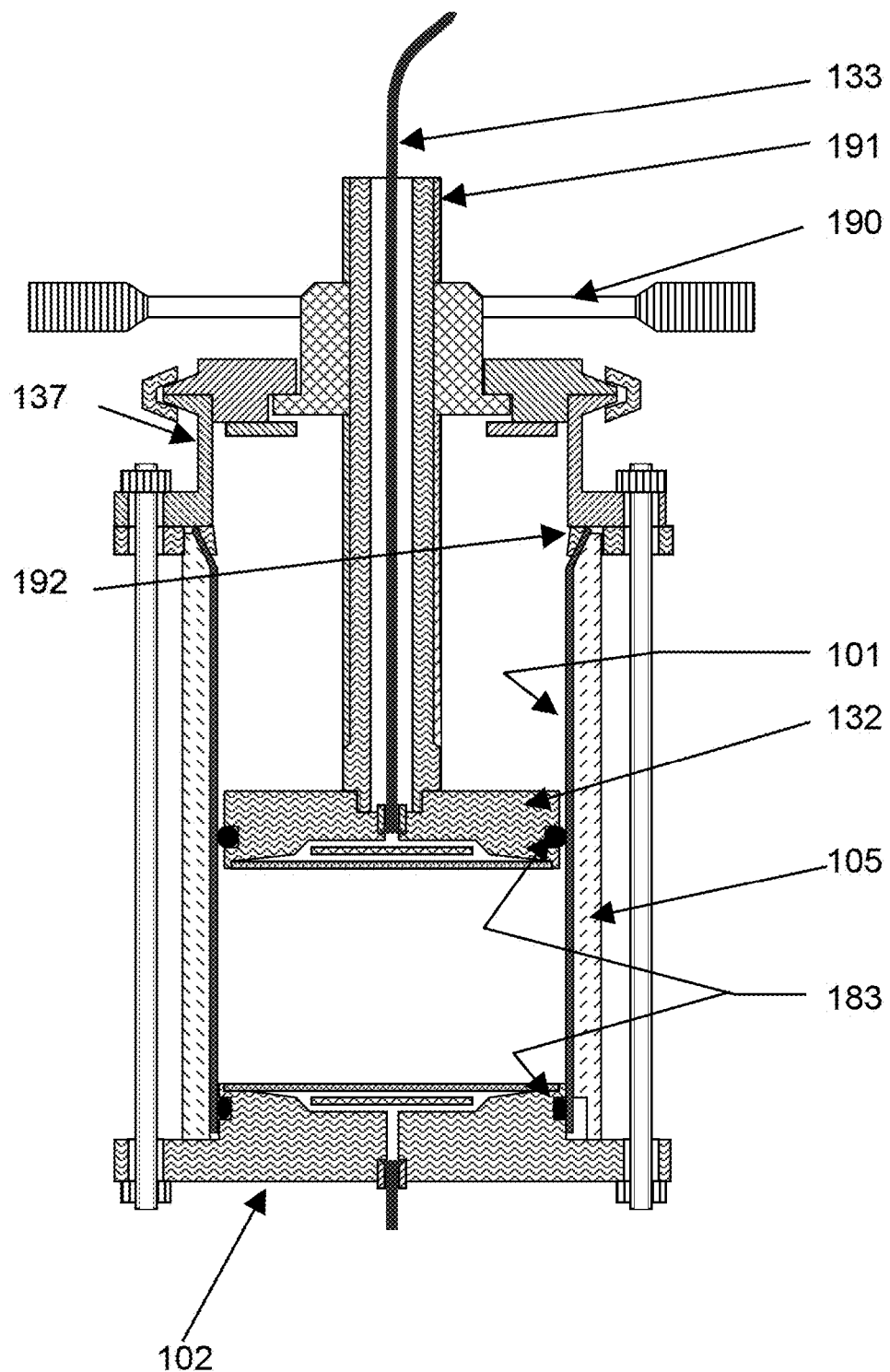
FIG. 22 shows a cross section of a column with tubular liner sealed via a gasket with the piston all along the column tube

The concept of column with liner can also be used in a more conventional chromatography column design such as the one depicted on FIG. 22. In this embodiment, the piston 132 encloses a seal 183 that can be for example an O-ring or any other seal including but not limited to a lobe joint or a scraper seal, as on FIG. 19. But contrarily to the previously-described designs where the column tube is made of 2 sections 106 and 105, in the embodiment of FIG. 22, the column tube is made of one cylindrical section 105 sufficiently tall to contain the volume of slurry. The piston 132 is tight all along the column tube 105. Being constantly submitted to the hydraulic pressure in the column, the piston 132 is held in place, for example, by being attached to a central screw 191 that can be raised or lowered by turning a central nut 190 pivoting in the cover 137. In the embodiment of FIG. 22, the liner is positioned in the tube 105 and retained on the upper edge of 105 by a wedge 192, or, if the liner is sufficiently soft, the liner can be tucked over a neck as depicted in former designs such as FIG. 18 or 19. One advantage of the embodiment depicted in FIG. 22 is that, for regulated products, the material of the column tube does not need to be validated for contact with drug or food. Of course, where the product is regulated, the liner will have such validation. This minimizes the use of costly high grade material.

Figure 23:
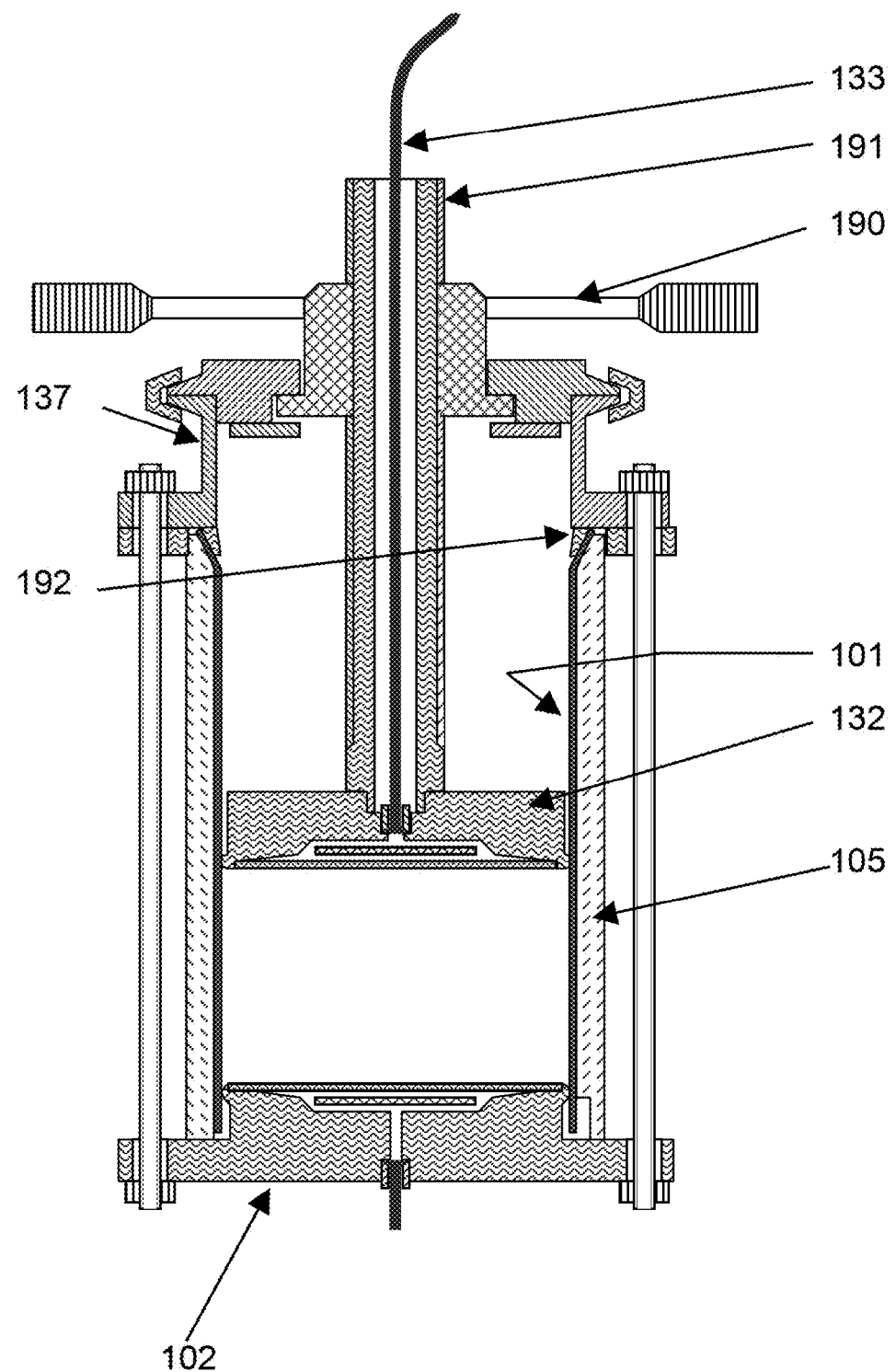
FIG. 23 shows the same view as FIG. 22, but an embodiment in which the piston and bottom directly seal against the tubular liner.

If the liner is sufficiently thick and soft, the column design can be simplified as depicted on FIG. 23. Compared to the FIG. 22, the sealing between the bottom plate 102 and the liner, as well as between the piston 132 and the liner 101 is obtained directly by mechanical compression, without seal such as 183 in FIG. 22. For minimizing the shear stress between the piston 132 (or bottom plate 102) and the liner 101, the outer edge of the piston and bottom plate can enclose a protuberance (for example, that is bead-shape), which ensures a smooth installation or movement of the piston 132 (or bottom plate 102) in the liner 101. In the embodiment of FIG. 23, the protuberance (which provides water tightness) is positioned at the same level as the filter. This ensures that the column inner volume is submitted to the flow of the mobile phase and reduces the risk of a dead spot in the column.

The methods and concepts described herein can also be used for preparing a compact and homogeneous bed made of particles for purposes other than chromatography. One example of such a purpose is filtering; another is use of the bed as a preliminary step for chromatography. For example, aspects of the invention can be used in fusing a bed of particles into a monolith structure by polymerization. Aspects of the invention can also be used for preparing chromatography media between the bottom and top plates inside the plastic film, with other media configurations, such as discs. Aspects of the invention is not limited to columns of circular cross section. By eliminating the need for dynamic sealing, the invention can easily be adapted to columns of virtually all cross section shapes, such as polygons, ellipses, etc. The tubular plastic film can also be an elastomeric film, such as EPDM or silicone.

Figure 24:
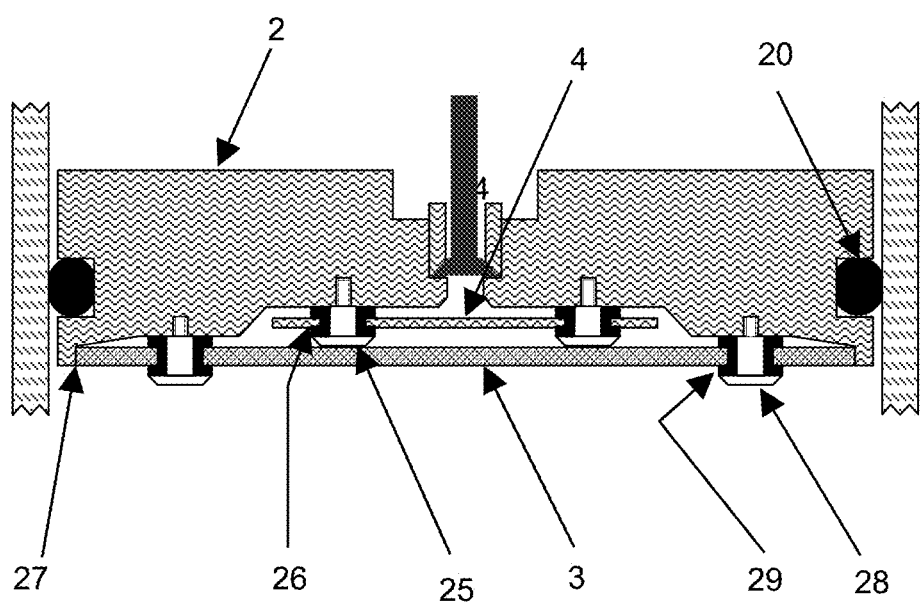
FIG. 24 depicts positioning of the filter in an opening comprising the bore of the piston.

As noted above, also provided herein is a method of applying a filter to a bore hole of a bottom plate of a chromatography column and/or piston for packing a chromatography column. This method can be applied in conjunction with the other methods described herein (e.g., use of a liner and/or percussive packing) or can be used in the absence of such methods. An embodiment is depicted in FIG. 24, which depicts positioning of the filter (3) in the bore of the piston. As noted elsewhere, the same action can be applied to fix a filter to the bore of the bottom plate. This fixing plays at least two roles: it serves as a sealing technique, to prevent the media from circumventing the filter and entering the distribution chamber behind the filter, and it serves as a mechanical fixing for holding the filter (3) in place while being submitted to the mobile flow. Indeed, when injecting a mobile phase downward, the flow resistance of the filter (3) due to its porous material is converted to an axial strength, which tends to push the filter (3) away from the piston. The filter (3) can be retained by its outer diameter, and eventually with additional fixings (fasteners) distributed on its surface. FIG. 24 depicts an embodiment in which filter screws (28) are sealed with filter screw gaskets (29). The filter screw gaskets (29) assist in preventing diffusion of liquid or contaminants in the thread of the screws. They also prevent the mobile phase from entering in the holes of the filter where filter screws (28) seat. As the fasteners can create local singularities in the distribution, their size and number can be minimized. In some embodiments, fasteners for holding the filter are not included at all where the fixing of the filter by shrinking is sufficient.

The shrinking technique employs the thermal expansion of materials such as polypropylene or polyethylene used for the piston (2) or bottom plate. The piston (2) and bottom plate enclose an opening (27) comprising the bore, the opening having a diameter slightly smaller than the filter at ambient temperature, and slightly larger or equal to filter diameter at higher temperature. For instance, polypropylene heated from 30° C. to 100° C. expands by around 1%. If needed, the filter can be cooled down so as to cumulate the thermal expansion of the filter or bottom plate bore with the thermal shrinkage of the filter material at cool temperature.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A chromatography column comprising:
   a rigid column shell,
   a bottom plate secured to said rigid column shell and comprising a layer of porous material covering a rigid and liquid-impermeable bottom plate base wherein said rigid and liquid-impermeable bottom plate base has a bottom plate port therein for passage of liquid,
   a piston comprising a filter covering a rigid and liquid-impermeable piston base and said rigid and liquid-impermeable piston base having a piston port for passage of liquid, said piston fitting within a tube within said rigid column shell, and
   said tube being of flexible, water-impermeable material containing and in contact with a separation medium, said tube being open at a first end such that the tube is in full contact with the rigid column shell, closed at a second end with said bottom plate, and encircling said piston.

2. The chromatography column of claim 1 further comprising a releasable seal between said tube and said piston.

3. The chromatography column of claim 2, wherein the piston comprises the seal.

4. The chromatography column of claim 2, wherein the rigid column shell comprises the seal.

5. The chromatography column of claim 2, wherein the seal is selected from the group consisting of an O-ring, a lobe joint, and a scraper seal.

6. The chromatography column of claim 1 wherein said flexible, waterimpermeable material is elastic.

7. The chromatography column of claim 1, wherein the rigid column shell has a height and the chromatography column further comprises a column shell extension removably attachable to said rigid column shell to extend an axial length of said rigid column shell, and wherein said tube of flexible, water-impermeable material is of sufficient length to extend through both said rigid column shell and said column shell extension, said column shell extension being of sufficient width to receive said piston with clearance between said piston and said column shell extension to allow liquid to flow past said piston and thereby equalize pressure above and below said piston when said tube of flexible, water-impermeable material is within both said rigid column shell and said column shell extension and said piston is moved within said tube.

8. The chromatography column of claim 7 further comprising a cap that attaches to said column shell extension and that supports said piston, and wherein said first end of said tube of flexible, water-impermeable material is secured to said cap.

9. The chromatography column of claim 8 further comprising a slurry injection port allowing for injection of a slurry of chromatography media under the piston in the chromatography _column.

10. The chromatography column of claim 1 further comprising under the rigid and liquid-impermeable base, a percussion table capable of rhythmically tapping the rigid and liquid-impermeable base to improve packing of particles of a separation medium in the chromatography column.

* * * * *